US012564736B2

(12) United States Patent
Humayun et al.

(10) Patent No.: US 12,564,736 B2
(45) Date of Patent: Mar. 3, 2026

(54) NON-INVASIVE ULTRASOUND NEUROMODULATION FOR VISION RESTORATION FROM RETINAL DISEASES

(71) Applicant: UNIVERSITY OF SOUTHERN CALIFORNIA, Los Angeles, CA (US)

(72) Inventors: Mark S. Humayun, Glendale, CA (US); Qifa Zhou, Los Angeles, CA (US); Xuejun Qian, Los Angeles, CA (US); Biju Thomas, Los Angeles, CA (US); Gengxi Lu, Los Angeles, CA (US); Koping Kirk Shung, Alhambra, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 0 days.

(21) Appl. No.: 18/272,774

(22) PCT Filed: Jan. 20, 2022

(86) PCT No.: PCT/US2022/013163
§ 371 (c)(1),
(2) Date: Jul. 17, 2023

(87) PCT Pub. No.: WO2022/159607
PCT Pub. Date: Jul. 28, 2022

(65) Prior Publication Data
US 2024/0149077 A1    May 9, 2024

Related U.S. Application Data

(60) Provisional application No. 63/140,730, filed on Jan. 22, 2021.

(51) Int. Cl.
*A61N 7/00*        (2006.01)

(52) U.S. Cl.
CPC ........ *A61N 7/00* (2013.01); *A61N 2007/0026* (2013.01); *A61N 2007/0056* (2013.01)

(58) Field of Classification Search
CPC .............. A61N 7/00; A61N 2007/0026; A61N 2007/0056; A61N 2007/0095; A61F 9/08; G06V 20/60; G06V 10/70
See application file for complete search history.

(56) References Cited

U.S. PATENT DOCUMENTS 7,079,900 B2 *   7/2006   Greenburg ......... A61N 1/36046
                                                               607/54
2009/0318853 A1 *  12/2009   Reed ........................ A61N 7/00
                                                               601/2

(Continued)

FOREIGN PATENT DOCUMENTS

CN        110167630 A      8/2019
WO          0015097 A2     3/2000

OTHER PUBLICATIONS

Artificial vision: what people with bionic eyes see (Year: 2017).*

(Continued)

*Primary Examiner* — Hien N Nguyen
(74) *Attorney, Agent, or Firm* — Snell & Wilmer LLP

(57)            ABSTRACT

Retinal disease is responsible for many instances of vision impairment. Often, individuals with vision impaired due to retinal disease continue to have functioning retinal neurons. Thus, systems, methods, and devices to stimulate retinal neurons may restore sight for vision-impaired individuals. Systems, methods, and devices provided herein direct ultrasound energy into retinal neurons and modulate phase and amplitude of ultrasound energy in time and space domains in order to variously stimulate various retinal neurons, generating neural responses consistent with visual reproduction of intended images.

12 Claims, 17 Drawing Sheets

(56) References Cited

U.S. PATENT DOCUMENTS

| | | | |
|---|---|---|---|
| 2010/0016719 A1* | 1/2010 | Freiburger | G01S 7/52096 |
| | | | 600/443 |
| 2013/0079621 A1 | 3/2013 | Shoham et al. | |
| 2013/0245505 A1* | 9/2013 | Khuri-Yakub | A61F 9/08 |
| | | | 601/2 |
| 2017/0246481 A1 | 8/2017 | Mishelevich | |
| 2019/0105517 A1 | 4/2019 | Tyler | |
| 2019/0105519 A1* | 4/2019 | Herekar | A61B 8/463 |

OTHER PUBLICATIONS

International Search Report and Written Opinion of the International Searching Authority, PCT/US2022/013163, mail date May 11, 2022, 9 pages.

\* cited by examiner

801

801

243 μm

Normalized Response

Normal

Medial

MEA

Caudal 1 mm

803

161 μm

257 μm

299 μm

184 μm

239 μm

188 μm

253 μm

804 spatial resolution

N_t = 12

Resolution (um)

rat #

1          #2          #3

1101

1203

1

NON-INVASIVE ULTRASOUND NEUROMODULATION FOR VISION RESTORATION FROM RETINAL DISEASES

CROSS-REFERENCE TO RELATED APPLICATIONS

This application is based upon and claims priority to U.S. provisional patent application 63/140,730 entitled "NON-INVASIVE ULTRASOUND NEUROMODULATION FOR VISION RESTORATION FROM RETINAL DISEASES" and filed on Jan. 22, 2021, the entire content of which is incorporated herein by reference.

STATEMENT AS TO FEDERALLY SPONSORED RESEARCH

This invention was made with government support under contract numbers R01EY032229, R01EY028662, R01EY030126 and P30EY029220 awarded by the National Institutes of Health (NIH). The government has certain rights in this invention.

BACKGROUND

1. Field

This disclosure relates generally to vision restoration technology, and more specifically, to ultrasound neuromodulation for vision restoration.

2. Description of the Related Art

Retinal degeneration involving progressive deterioration and loss of function of photoreceptors is a major cause of permanent vision loss worldwide. Strategies to treat these incurable conditions incorporate retinal prostheses via electrically stimulating surviving retinal neurons with implanted devices in the eye, optogenetic therapy and sonogenetic therapy. Existing challenges of these strategies include their invasive character, complex implantation surgeries, and risky gene therapy. Thus, there is a need for systems and methods of non-invasive retinal stimulation.

SUMMARY

A portable ultrasonic neuromodulation system for vision restoration from retinal diseases is provided. The system may have a camera. The camera may capture an image of an object. The system may also have a processor. The processor may receive the captured image and transfer data corresponding to the captured image to an ultrasound system. The system may have an ultrasound system. The ultrasound system may convert the data corresponding to the image to an acoustic beam pattern. The acoustic beam pattern may correspond to the image. Thus, the ultrasound system may include an ultrasound transducer. The ultrasound transducer may deliver acoustic energy at a retina of an eye to evoke a neural response corresponding to the image.

The system may have further aspects in various embodiments. For instance, the system may include a sensor configured to monitor the neural response provide data corresponding to the neural response to the processor. The ultrasound transducer of the system may be 2D matrix array of transducer elements. The system may include a power amplifier. The power amplifier may drive each individual element of the 2D matrix array of the transducer elements.

The system may have aspects configured to generate different acoustic beam patterns with different characteristics. For instance, the transmitted acoustic beam pattern may have a negative peak acoustic pressure of between 0.1 MPa to 15 MPa. In various embodiments, the transmitted acoustic beam pattern may have a negative peak acoustic pressure of between 0.1 MPa to 10 MPa. The transmitted acoustic beam pattern may be generated for a duration of between 0.1 to 500 milliseconds, and with the duty cycle between 10% to 90%. In various instances, the duty cycle may be between 0.1% to 100%, or another range. The acoustic beam pattern may have a negative peak acoustic pressure that is between 0.5 MPa to 3 MPa (MI: 0.2-1.7) and that is generated for a duration of between 5 to 300 milliseconds. In various embodiments, the acoustic beam pattern has a center frequency of between 1-50 MHz. In various embodiments, the acoustic beam pattern has a center frequency of between 3-24 MHz.

A method of vision restoration from retinal diseases is also provided. The method may include capturing, using a camera, an image of an object. The method may include receiving, at a processor, the captured image and transferring, by the processor, the captured image to an ultrasound system. The method may include converting, by the ultrasound system, the captured image to an acoustic beam pattern and transmitting, by the ultrasound system, the acoustic beam pattern to deliver energy to an eye. In various embodiments, the energy evokes neuron activity in a retina of the eye.

Different embodiments of the method may include various features. For example, the ultrasound system may have a 2D matrix array of transducer elements and transmitting the acoustic beam pattern may include modulating both amplitude and phase for each individual element of the 2D matrix array of transducer elements to produce the acoustic beam pattern. The ultrasound system may include a power amplifier configured to drive each individual element of the 2D matrix array of transducer elements.

The method may include generating acoustic beams with different characteristics. For instance, the transmitted acoustic beam pattern may have a negative peak acoustic pressure of between 0.1 MPa to 15 MPa. In various embodiments, the acoustic beam pattern may have a negative peak acoustic pressure of between 0.1 MPa to 10 MPa and may be generated for a duration of between 0.1 to 500 milliseconds, with a duty cycle between 10% to 90%. In various instances, the duty cycle may be between 0.1% to 100%, or another range. The acoustic beam pattern may have a negative peak acoustic pressure that is between 0.5 MPa to 3 MPa (MI: 0.2-1.7) and may be generated for a duration of between 5 to 300 milliseconds. In various embodiments, the acoustic beam pattern has a center frequency of between 1-50 MHz. The acoustic beam pattern may have a center frequency of between 3-24 MHz.

A portable ultrasonic neuromodulation system is provided. The system may be for vision restoration from retinal diseases. The system may have a sensor. The sensor may monitor neural response of a brain. The system may have a processor. The processor may be configured to generate an image and transfer data corresponding to the image to an ultrasound system. The ultrasound system may be configured to convert the data corresponding to the image to an acoustic beam pattern corresponding to the image. The ultrasound system may have a ultrasound transducer having a 2D matrix array of transducer elements. The 2D matrix array of transducer elements may generate an acoustic beam pattern via modulation of both amplitude and phases information for each transducer element to deliver acoustic energy at a retina of an eye of a blind patient to evoke neural response. The sensor may measure the neural response and may instruct the processor to alter the acoustic beam pattern to cause the neural response to correspond to the image. The ultrasound system may further include a power amplifier connected to and driving each transducer element of the 2D matrix array of transducer elements.

In various embodiments of the system, the transmitted acoustic beam pattern may have various aspects. For instance, the transmitted acoustic beam pattern may have a negative peak acoustic pressure of between 0.1 MPa to 15 MPa. In various embodiments, the transmitted acoustic beam pattern may have a negative peak acoustic pressure of between 0.1 MPa to 10 MPa. The transmitted acoustic beam pattern may be generated for a duration of between 0.1 to 500 milliseconds and with a duty cycle between 10% to 90%. In various instances, the duty cycle may be between 0.1% to 100%, or another range. The acoustic beam pattern may have a negative peak acoustic pressure that is between 0.5 MPa to 3 MPa and may be generated for a duration of between 5 to 300 milliseconds. In various embodiments, the acoustic beam pattern has a center frequency of between 1-50 MHz. In various instances, the acoustic beam pattern has a center frequency of between 3-24 MHz.

BRIEF DESCRIPTION OF THE DRAWINGS

Other systems, methods, features, and advantages of the present invention will be or will become apparent to one of ordinary skill in the art upon examination of the following figures and detailed description.

DETAILED DESCRIPTION

Figure 1A:
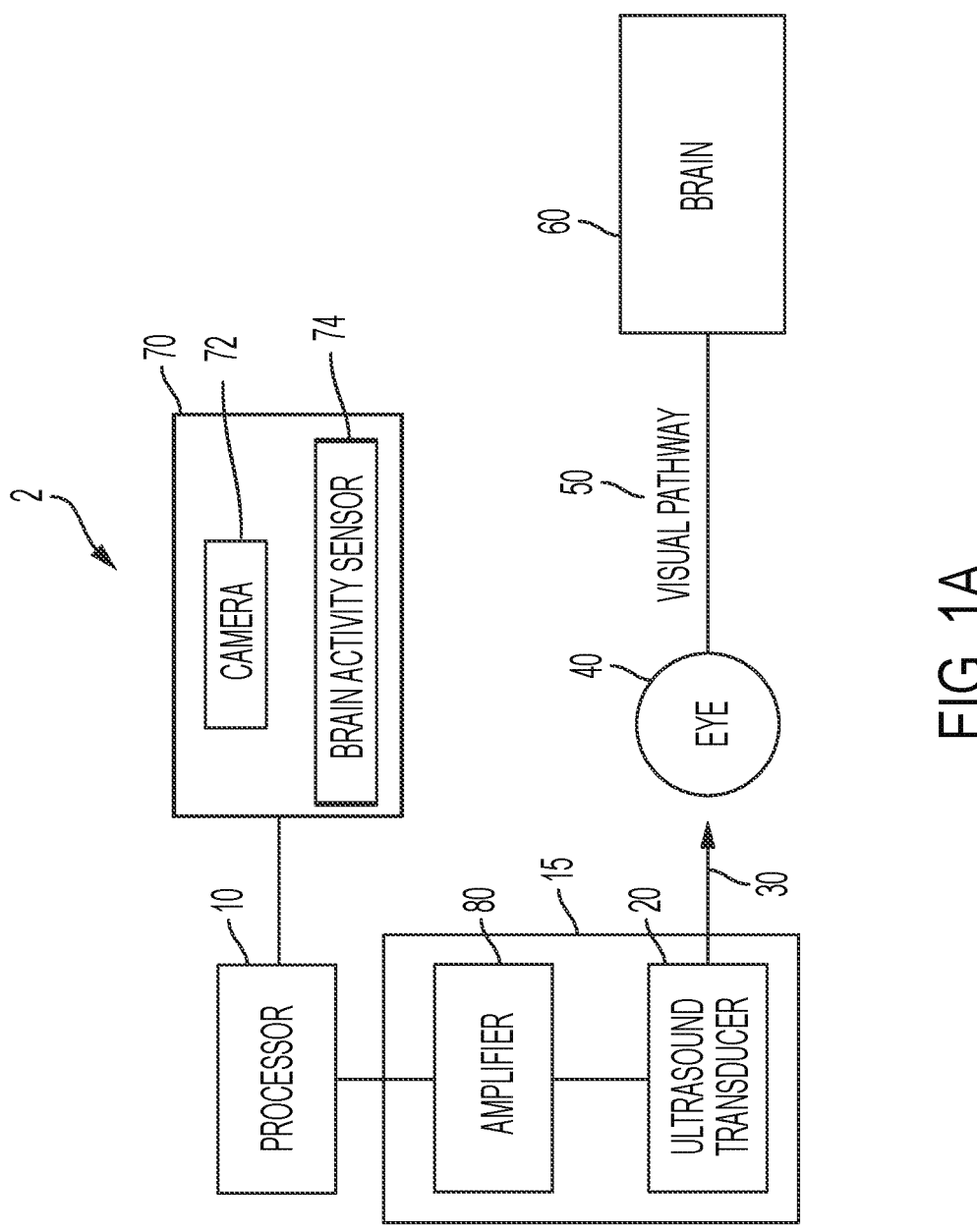
FIG. 1A depicts a portable ultrasonic neuromodulation system, in accordance with various embodiments.

Retinal degeneration involving progressive deterioration and loss of function of photoreceptors is a major cause of permanent vision loss worldwide. Strategies to treat these incurable conditions incorporate retinal prostheses via electrically stimulating surviving retinal neurons with implanted devices in the eye, optogenetic therapy and sonogenetic therapy. Existing challenges of these strategies include their invasive nature, complex implantation surgeries, and risky gene therapy. Systems and methods are provided herein, along with experimental and other evidence and data, to provide that direct ultrasound stimulation on a retina can evoke neural response from the visual centers including the superior colliculus and the primary visual cortex (V1), in either normal-sighted or retinal degenerated eyes.

Various experiments involving blind rats in vivo are discussed herein. The neural response induced by the customized spherically focused 3.1-MHz ultrasound transducer has shown both good spatial resolution of 250 μm and temporal resolution of 5 Hz in the rat visual centers. An additional customized 4.4-MHz helical transducer was further implemented to generate static stimulation pattern of letter forms. Ultrasound stimulation of the retina in vivo is a safe and effective approach with high spatiotemporal resolution. Ultrasound stimulation provides a novel and non-invasive visual prosthesis for translational applications in blind patients.

Retinal degenerative diseases, caused by progressive degeneration of the light-sensitive photoreceptors in the retina, is one of the major causes of vision loss and blindness worldwide. Despite the loss of sensitivity to light, the remaining visual pathway is mostly intact and functional, allowing the visual prostheses to emerge as tools to restore vision. Microelectronic retinal prosthetics attempt to restore vision by bypassing the damaged photoreceptors and directly stimulating the inner retinal neurons. With the rapid development of electronic technology, some of these devices have been translated from the laboratory to the clinic and been successfully implanted in patients, such as Argus II device. However, the challenges of the invasive implant of electronic devices, limited amounts of electrodes, considerable surgical costs and potential surgery side-effects have remained unsolved. To conquer these challenges, many efforts have been recently made, including the investigation of optogenetics, near-infrared sensors, sonogenetics and gene therapy. Although favorable results have been reported, all these methods still require risky invasive procedures and comprehensive gene engineering. Therefore, an approach which can apply directly on the naturally existing mechanoreceptors to recover visual function in blind patients is desired.

Ultrasound (US) has been widely used in the clinic as a non-invasive approach for diagnostic imaging and therapeutic applications. Ultrasound also has the ability to modulate the central nervous system. With the attractive features of noninvasiveness, deep penetration to cover the whole brain, and spatial selectivity on the order of sub-millimeters, ultrasound neuromodulation systems and methods provided herein enable non-invasive stimulation of retinal neurons.

Systems and methods herein provide for in vivo demonstration of vision restoration and potential pattern generation (e.g., letter forms) from retinal degenerative models (e.g., blind animal cases) at a high spatiotemporal resolution. Ultrasound stimulation thus provides an efficient vision restoration approach.

With attention to FIG. 1A, a portable ultrasonic neuromodulation system 2 is provided. The system is operable to provide vision restoration from retinal diseases. The system 2 may generate ultrasonic signals, direct these signals to an eye, causing the signals to stimulate retinal neurons. The retinal neurons send signals along visual nerve pathways to a brain, which perceives visual input such as letters, numbers, shapes, and other visual patterns and features. The system may also include a brain activity sensor that monitors neural response and allows calibration and adjustment of the ultrasonic signals to better reproduce desired neural functions, such as to tune the ultrasonic signals to produce more accurate and precise reproductions of desired imagery in the vision function of a particular user's nervous system.

In various embodiments, the system 2 includes a sensor 70. A sensor 70 may be configured to receive information from an environment. For example, the sensor 70 may comprise a camera 72 configured to capture an image of an object seen by a human. The camera may be a visual light camera, or an infrared camera, or an ultraviolet camera, or any other type of camera as desired. Moreover, the sensor 70 may be a different type of sensor other than a camera. In various embodiments, the sensor 70 includes a brain activity sensor 74. The brain activity sensor 74 detects electrical impulses within a brain 60, for instance, to monitor brain response to various stimulation in order to facilitate guidance of the stimulation, improvement and calibration of a system 2, and experimentation. The sensor 70 may be an array of sensors. For instance, the sensor 70 may include both a brain activity sensor 74 and a camera 72, thus being an array of sensors. Additional or different sensing components may be incorporated as desired.

The sensor 70 may be connected to a processor 10. The processor 10 is a computer configured to receive inputs and generate outputs. For instance, the processor 10 may generate signals or data corresponding to a desired ultrasound waveform, duty cycle, amplitude, frequency, modulation, or other characteristics. The processor 10 may communicate these signals and data to an ultrasound system 15. The ultrasound system 15 may generate one or more acoustic beam to stimulate an eye 40 in response to the signals or data. In various instances, the one or more acoustic beam may stimulate the eye 40 in such a way as to cause the brain 60 to perceive an image. The image may be captured by the sensor 70 (e.g., camera 72). In further instances, the one or more acoustic beam may stimulate the eye 40 in such a way as to cause the brain 60 to perceive an image loaded from computer memory by the processor 10. Moreover, the sensor 70 may monitor brain activity to evaluate whether the brain 60 exhibits activity consistent with the reproduction of the image as desired, or if changes to the one or more acoustic beam may be effectuated. Thus, the brain activity sensor 74 may be utilized to fine tune the ultrasound waveform associated with the one or more acoustic beam according to specific physiology of a specific user to more accurately and precisely reproduce neural responses consistent with a non-impaired eye viewing the image captured by the camera 72.

Figure 2:
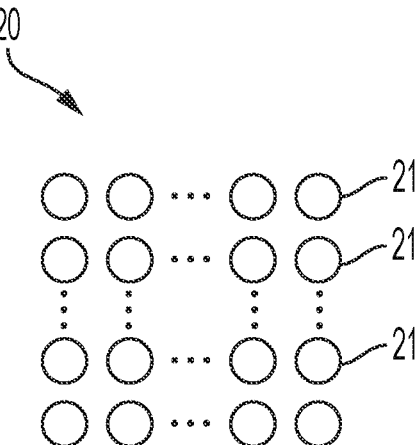
FIG. 2 depicts an example ultrasound transducer comprising an array of transducer elements and for use in the portable ultrasonic neuromodulation system, in accordance with various embodiments.

As mentioned, the ultrasound system 15 may generate one or more acoustic beam. In various instances, the ultrasound system 15 has an ultrasound transducer 20 that generates the one or more acoustic beam. The ultrasound transducer 20 is a device configured to convert data or signals into acoustical energy. In various instances, an amplifier 80 is provided between the processor 10 and the ultrasound transducer 20. The amplifier 80 may generate waveforms having sufficient amplitude, phase, bandwidth, center frequency, and other acoustic properties to cause the ultrasound transducer 20 to generate a desired acoustical beam. With brief reference to FIG. 2, in various instances, the ultrasound transducer 20 comprises an array of transducer elements 21. As such, the amplifier 80 may generate multiple waveforms having multiple different acoustic properties, such as to cause the ultrasound transducer 20 to generate one or more acoustical beam, or to steer one or more acoustical beam, in order to stimulate different retinal neurons of the eye 40 differently, facilitating reproduction by the brain 60 of complex patterns, colors, images, shapes, and/or the like.

Thus, a portable ultrasonic neuromodulation system 2 for vision restoration from retinal diseases may include the sensor 70 such as a camera 72. The camera 72 may be configured to capture an image of an object seen by a human. The system 2 may include a processor 10. The processor 10 may be configured to receive the captured image and to transfer data corresponding to the captured image to an ultrasound system 15. The ultrasound system 15 have an ultrasound transducer 20. The ultrasound transducer may be configured to convert the data corresponding to the image to an acoustic beam pattern 30 corresponding to the image and transmit the acoustic beam pattern 30 via the modulation of both amplitudes and phases information for each individual element 21 (FIG. 2) of the customized ultrasound 2D matrix array (ultrasound transducer 20) in order to deliver a specific acoustic energy distribution at a retina of an eye 40 of a blind patient to evoke a neural response corresponding to the image. The neural response may communicate along a visual pathway 50 to a brain 60 to generate a corresponding pattern, color, image, shape, and/or the like. The ultrasound system 15 may also have an amplifier 80. The amplifier 80 may be a power amplifier configured to drive each individual element 21 (FIG. 2) of the ultrasonic 2D matrix array (ultrasound transducer 20).

In another variation, the portable ultrasonic neuromodulation system 2 for vision restoration from retinal diseases may include the sensor 70 (e.g., brain activity sensor 74) configured to monitor neural responses of a brain 60. The system 2 may include a processor 10. The processor 10 may be configured to generate an image and to transfer data corresponding to the generated image to an ultrasound system 15. The ultrasound system 15 have an ultrasound transducer 20. The ultrasound transducer may be configured to convert the data corresponding to the image to an acoustic beam pattern 30 corresponding to the image. The ultrasound transducer 20 may include a 2D matrix array of transducer elements 21 that generate the acoustic beam pattern 30 via modulation of both amplitude and phase information for each transducer element. In this manner, acoustic energy is delivered at a retina of an eye 40 of a blind patient to evoke neural responses. The sensor may measure the neural responses and may instruct the processor to alter the acoustic beam pattern to cause the neural response to correspond to the image.

The transmitted acoustic beam pattern 30 may have a variety of specific aspects. For instance, the pattern 30 may have a negative peak acoustic pressure of between 0.1 MPa to 15 MPa. In various embodiments, the pattern 30 may have a negative peak acoustic pressure of between 0.1 MPa to 10 MPa (corresponding to a Mechanical Index: 0.1-15 based on the center frequency of the ultrasound probe). The pattern 30 may be generated for a duration of between 0.1 to 500 milliseconds. The pattern 30 may be generated with a duty cycle between 0.1% and 100%. In further instances, the pattern 30 is generated with a duty cycle between 10% to 90%. The acoustic beam pattern 30 may have a negative peak acoustic pressure that is between 0.5 MPa to 3 MPa (MI: 0.2-1.7). In various embodiments, the acoustic beam pattern 30 is generated by the ultrasound system 15 for a duration of between 5 to 300 milliseconds. In various embodiments, the acoustic beam pattern has a center frequency of between 1-50 MHz. The acoustic beam pattern 30 may have a center frequency of between 3-24 MHz.

As the transmitted acoustic beam pattern 30 stimulates the eye 40, the ultrasonic 2D matrix array (ultrasound transducer 20) may have a dual role in the vision restoration process. For instance, the ultrasonic 2D matrix array (ultrasound transducer 20) may serve as an imaging mode to visualize the morphological structure of the whole eye, which is in order to localize the region of interest, like the specific area of the retina. The ultrasonic 2D matrix array (ultrasound transducer 20) may have a further role such as a neuromodulation mode. The ultrasonic 2D matrix array (ultrasound transducer 20) will transmit the acoustic beam pattern at a certain energy level to evoke the neuron activity as mentioned.

Figure 1B:
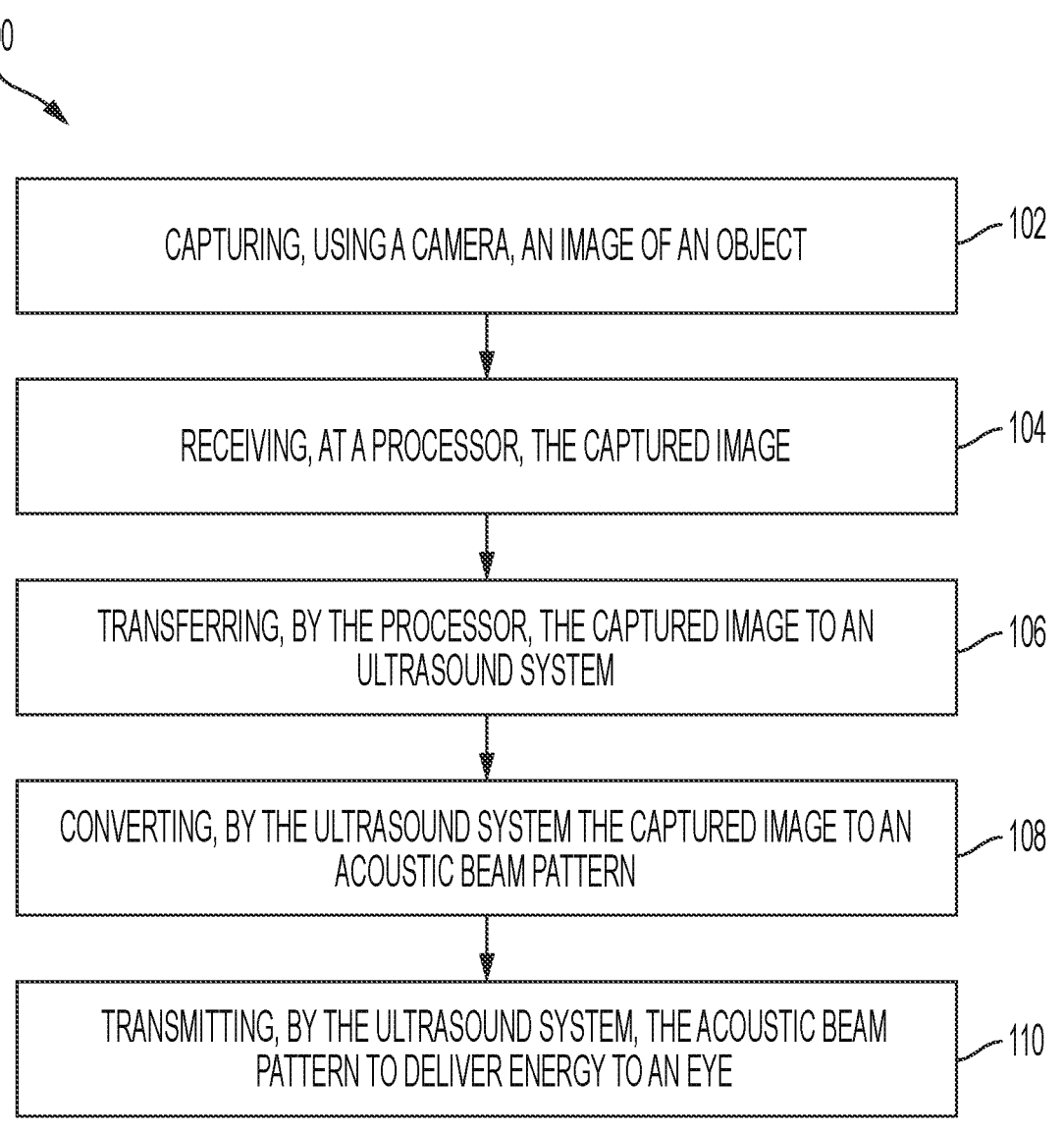
FIG. 1B depicts a method of vision restoration by the portable ultrasonic neuromodulation system, in accordance with various embodiments.

Having discussed the system 2, attention is now directed to FIG. 1B and a method of vision restoration 100 by the portable ultrasonic neuromodulation system. The method may facilitate restoration of vision from retinal diseases. In various embodiments, the method includes capturing, using a sensor such as a camera, an image of an object (block 102). The object may be an object that would be seen by a human if vision was not impaired. The method may include receiving, at a processor, the captured image (block 104). The processor may transfer the captured image to an ultrasound system (block 106). For instance, the captured image may be transferred to the ultrasound system for pattern conversion to produce an acoustic beam pattern. The ultrasound system may convert the captured image to an acoustic beam pattern (block 108). The ultrasound system may transmit the acoustic beam pattern to deliver energy to an eye (block 110). This energy may stimulate retinal neurons of the eye, causing a person having the eye to perceive an image. In various instances, the ultrasound system transmits the acoustic beam pattern by modulating both amplitude and phase information for each individual element of the customized ultrasound 2D matrix array in order to deliver a specific acoustic energy distribution at a retina of an eye of a blind patient to evoke neuron activity.

In various embodiments, the system and method are applied in animal contexts. For instance, extensive demonstrations are provided in the following paragraphs and in connection with rats having normal vision, and rats having impaired vision. In such animal scenarios, sensor 70 comprises a brain activity sensor 74 monitoring brain 60 activity and not a camera 72, though either or both sensor types may be implemented in further embodiments. The images are loaded by the processor 10 from a memory, though other architectures are contemplated. Thus, with ongoing reference to FIGS. 1A-B and 2, but with additional reference to FIG. 3 a demonstration is provided using ultrasound to induce neural response in Royal College of Surgeons (RCS) rats in vivo. In this manner, a retinal degenerative animal model widely used for assessing therapeutic effects is utilized for assessing therapeutic effects of systems and methods disclosed herein.

This demonstration shows that ultrasound stimulation reliably activates the degenerative retina in vivo with a high spatiotemporal resolution while light stimulation failed to show any retinal responses. This demonstration shows that ultrasound stimulation of the retina can evoke neural response in the contralateral visual pathways including the superior colliculus (SC) and the visual cortex (VC) of the brain. Based on the retinotopic map properties of the SC, this study deciphers the static stimulation pattern of letter forms of ultrasound-induced visual activities in the retina. Moreover, the discussion herein establishes the ultrasound-based non-invasive visual prosthesis as an appropriate vision restoration approach via the investigation of its standards of safety.

Figure 3:
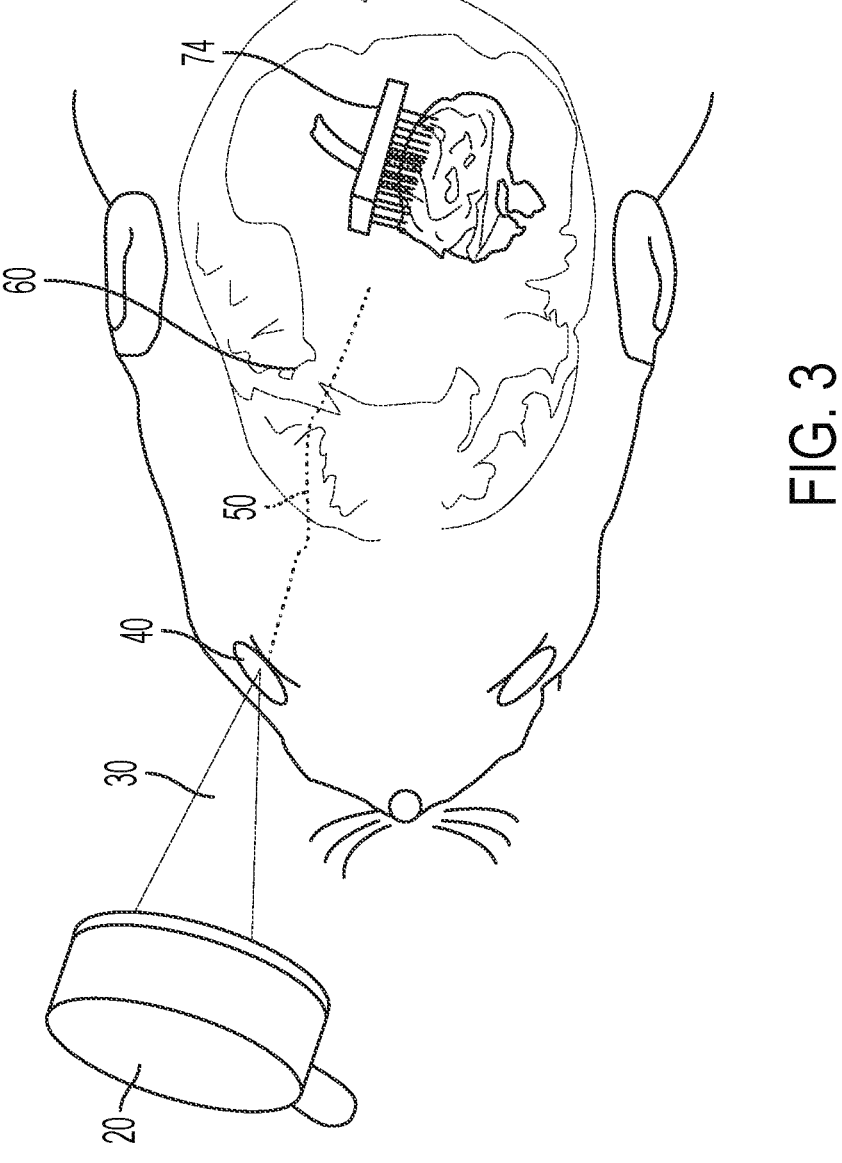
FIG. 3 depicts a demonstration of ultrasonic stimulation to induce neural response, in accordance with various embodiments.

With reference to both FIGS. 1A and FIG. 3, a system 2 is illustrated as implemented with rats. The custom-build ultrasound transducer 20 has a center frequency of 3.1 MHz with a focal depth of 10 mm. The characterization of the ultrasound transducer 20 was performed by a calibrated hydrophone. To be specific, the full-width-half-maximum (FWHM) beamwidth and the depth of focus (DOF) of the ultrasound transducer are 590 μm and 4400 μm, respectively. The free-field negative peak pressure (NPP) at the focal point, which is linearly related to the driving voltage of the ultrasound transducer, was measured to calculate the corresponding mechanical index (MI). To further investigate the effect of ultrasound attenuation and ultrasound-induced temperature change generated by the eye 40 structure, both a finite element analysis (FEA) and an ex vivo experimental test were conducted in this study. The FEA analysis implied that the eye 40 structure generated –2.0 dB attenuation while the attenuation of –3.3±0.4 dB was measured in the ex vivo test. These results were in line with expectations since the backside sclera at ex vivo condition would contribute to a higher attenuation. In terms of ultrasound-induced temperature rising under the ultrasound parameters of 2.83 MPa NPP and 200 ms ultrasound duration, ex vivo experimental measurement was consistent with the simulation study (that is 2° C. in simulation and 1.8° C. in the experiment). A 3.1 MHz spherically focused single-element transducer 20 was used to transmit acoustic waves (acoustic beam pattern 30) targeting at the retina of the eye 40. Retinal neurons were excited and then generated neural signals transmitting through the optic nerve (visual pathway 50) to the brain 60. A multielectrode array (MEA) (brain activity sensor 74) was inserted into the contralateral superior colliculus (SC) or visual cortex (VC).

Figure 4A:
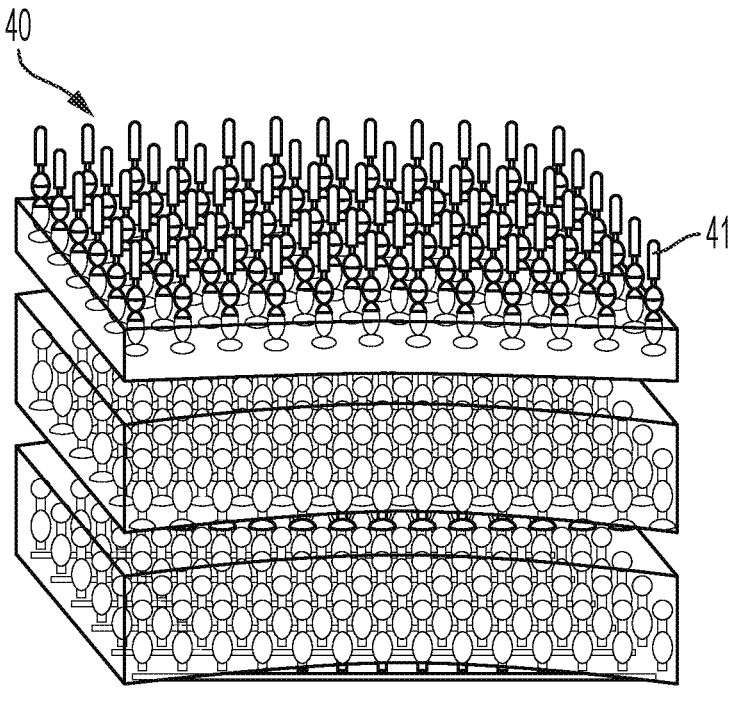
FIG. 4A depicts eye tissue structures associated with normal vision, in accordance with various embodiments.
Figure 4B:
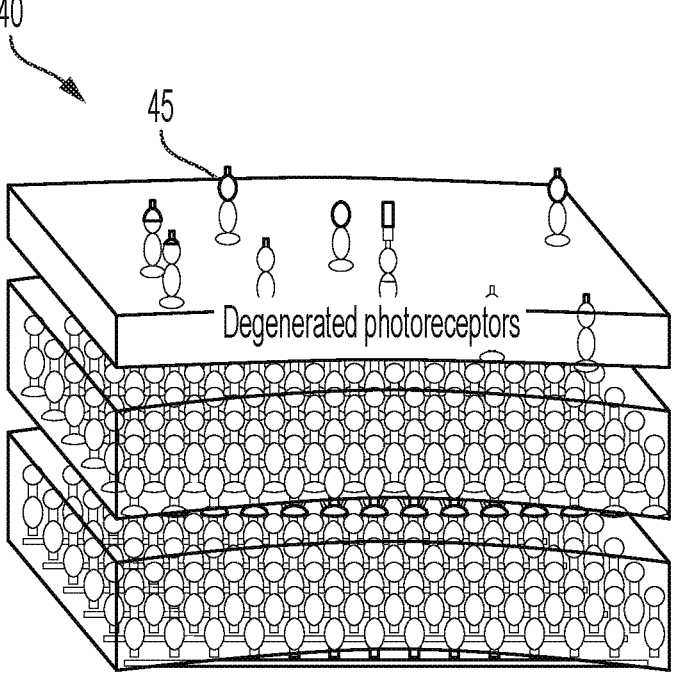
FIG. 4B depicts eye tissue structures associated with impaired vision, in accordance with various embodiments.

With reference to FIGS. 4A-B, eye tissues associated with normal vision and eye tissues associated with impaired vision are illustrated. FIG. 4A depicts eye tissue structures associated with normal vision. FIG. 4B depicts eye tissue structures associated with impaired vision. Prior to conducting the ultrasound stimulation experiments, the vision of rats was evaluated using full-field light stimulation. Some rats were verified to have normal vision, having eyes 40 with healthy photoreceptors 41 and other rats were verified to have impaired vision (e.g., to be blind) having eyes 40 with degenerated photoreceptors 45.

Figure 5A:
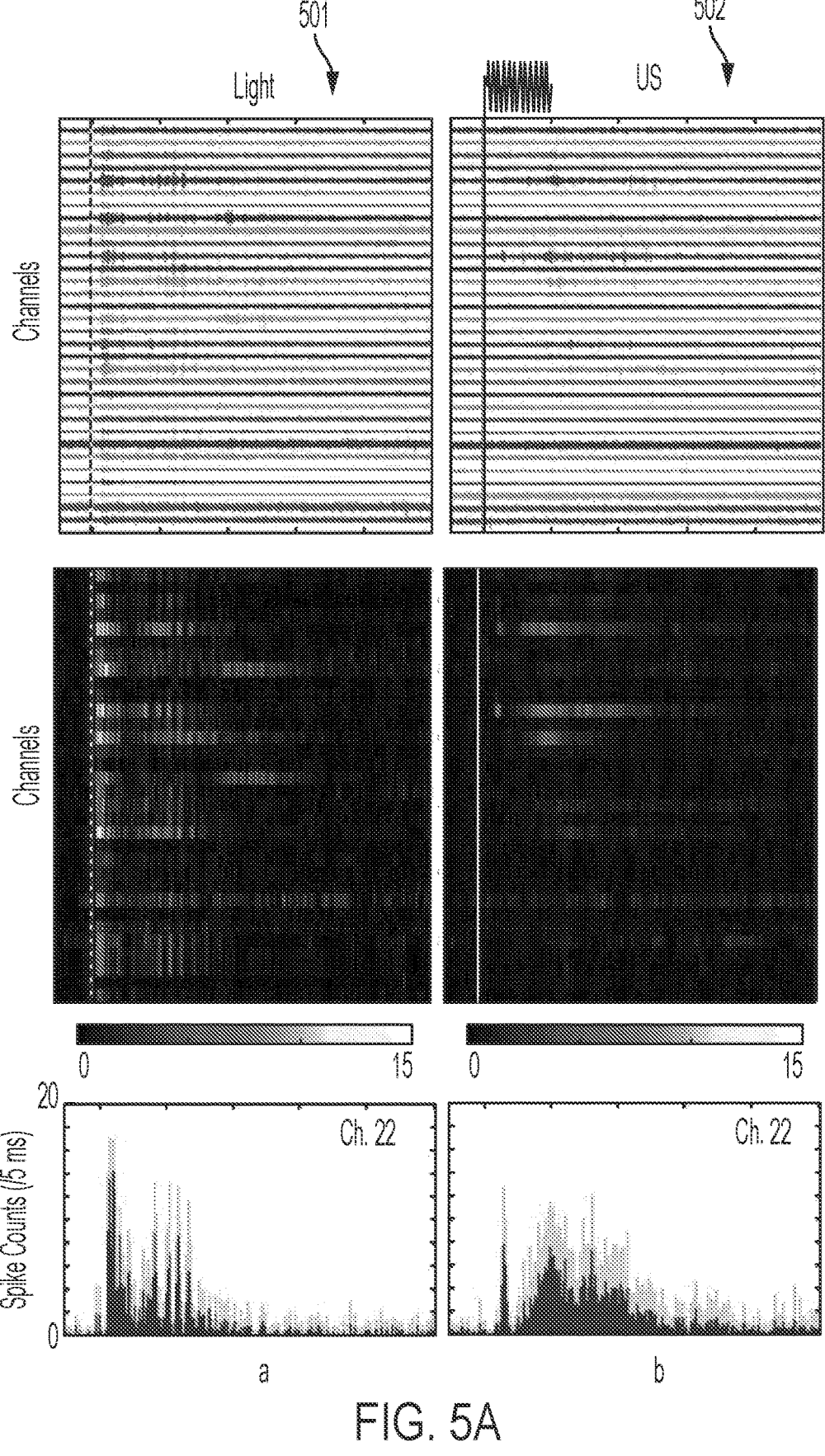
FIG. 5A shows charts corresponding to various stimuli and neural response evoked by light stimuli and ultrasonic stimuli for eyes with normal vision, in accordance with various embodiments.
Figure 5B:
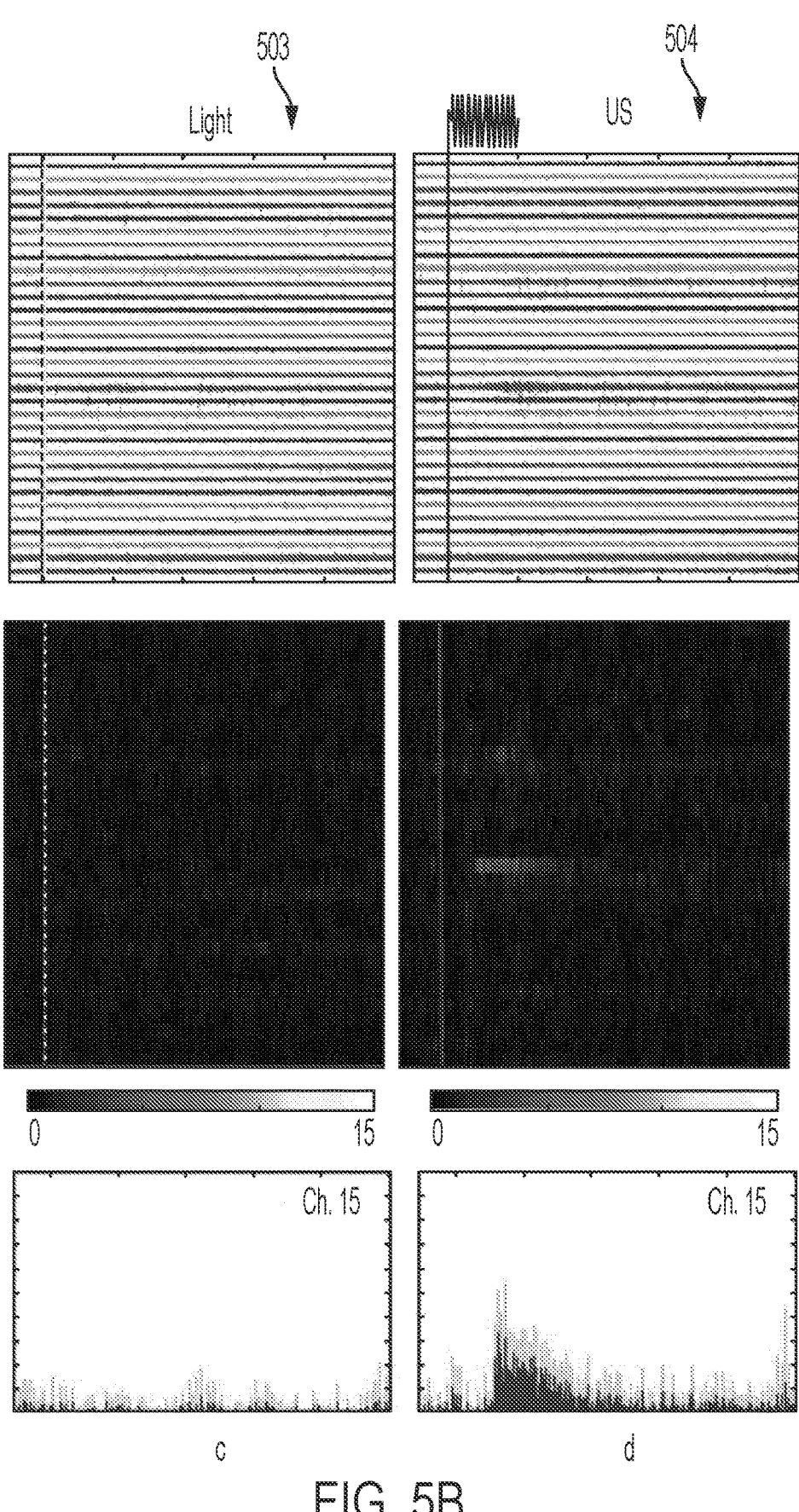
FIG. 5B shows charts corresponding to various stimuli and neural response evoked by light stimuli and ultrasonic stimuli for eyes with impaired vision, in accordance with various embodiments.

For the purpose of electrophysiological recording from the visual centers, the contralateral area of the skull was removed by a partial craniotomy. The neural response evoked by the light stimuli were recorded using a 32-channel multichannel electrode array (MEA) placed either on the VC (V1 area) or inside the surface layer of the superficial SC (~150 um depth) after removing the overlying VC area. FIGS. 5A-B show the collected results. FIG. 5A shows charts corresponding to various stimuli and neural response evoked by light stimuli and ultrasonic stimuli for eyes with normal vision. FIG. 5B shows charts corresponding to various stimuli and neural response evoked by light stimuli and ultrasonic stimuli for eyes with impaired vision. Referring to both FIGS. 5A-B, charts 501 show robust visual activities in response to light stimulation in normal-sighted rats. Charts 503 show that in retinal degenerate RCS rats, no such light-evoked visual activities were noticed.

For the in vivo ultrasound stimulation experiments, the ultrasound transducer is driven by a power amplified sinusoid tone burst signal and is placed in front of the rat eye and coupled with de-gassed gel. In both normal-sighted rats and in RCS blind rats, prior to stimulating the eyes, the ultrasound stimulation beam was directed away from the eyeball to conduct control experiments to examine off-target effects. As expected, no responses were observed in such control experiments, indicating that there are no potential electrical or auditory confounds.

To demonstrate whether ultrasound stimulation is an efficient tool in evoking neural response of the rats in vivo, 10 normal-sighted LE rats (SC recordings were conducted in 8 rats, and VC recording were conducted in 2 rats) were used. Examples of the ultrasound-evoked neural response recorded from the SC and VC of normal-sighted rats are shown in FIGS. 5A-B. Chart 502 illustrates the ultrasound-evoked neuron activity of normal-sighted rats. Unlike light-evoked spike activities in chart 501 that constantly appeared after a short latency for most of the recording channels, the ultrasound-evoked spike activities were observed only in comparatively few channels. This is because that the light stimulator used in this study was a full-field strobe flash, the light stimulation is capable to activate the entire retina, resulting in neural responses from almost all the recording channels. By contrast, the ultrasound-stimulated region of interest (ROI) determined by the focal zone of the ultrasound transducer is relatively small (at a few hundred microns level). As a consequence, as observed in charts 502, only a few MEA channels that presumably corresponded to the ultrasound stimulated region of the retina showed spike activities. In FIGS. 5A-B, the charts illustrate 500-7000 Hz bandpass filtered signals with a scale of ±80 μV in a recording time ranging from –0.1 s to 1 s, the average spike counts per 5 ms of all channels, and a representative channel that was randomly selected to demonstrate the spike counts curve (with both average value and standard deviation).

It should be noted that, despite the variation in the degree of ultrasound-evoked neural response between rats, all the normal-sighted rats showed neural response comparable to the responses during light stimulation. Results in normal-sighted rats indicated that ultrasound can be an approach to stimulate the retina in vivo.

To further validate the advantage of using ultrasound stimulation for vision restoration, a rat model of retinal degenerative blindness was investigated. The RCS rats that are considered to be totally blind after the age of 6 months were used in this study. To ensure a fair comparison with normal-sighted rats, same ultrasound stimulation parameters (e.g., intensity and duration) were used in both study groups. Chart 503 illustrates the null response to visual light stimulation by the blind rats, confirming their vision impairment. Chart 504 shows the ultrasound-evoked neural response in blind rats.

More specifically, based on the results from 16 RCS blind rats (14 rats for SC recording and 2 rats for VC recording), it is demonstrated that ultrasound is capable to stimulate the retinal neurons as evidenced by neural signals from the SC as shown in chart 504 and VC. Based on the response amplitude and response duration, the ultrasound-induced neural response in blind rats were generally weak compared to the responses from normal-sighted rats.

The influence of ultrasound intensity and ultrasound duration, the two major ultrasound stimulation parameters that showed substantial influence on evoked neural response, were further investigated. To conform with the U.S. Food and Drug Administration (FDA) recommendations on maximal MI of 1.9, which corresponds to an NPP of 3.35 MPa at 3.1 MHz, the experiment varied the driving voltage of the ultrasound transducer from 200 mV (that is 1.29 MPa in NPP) to 600 mV (that is 3.37 MPa in NPP) with an interval of 50 mV.

Figure 6:
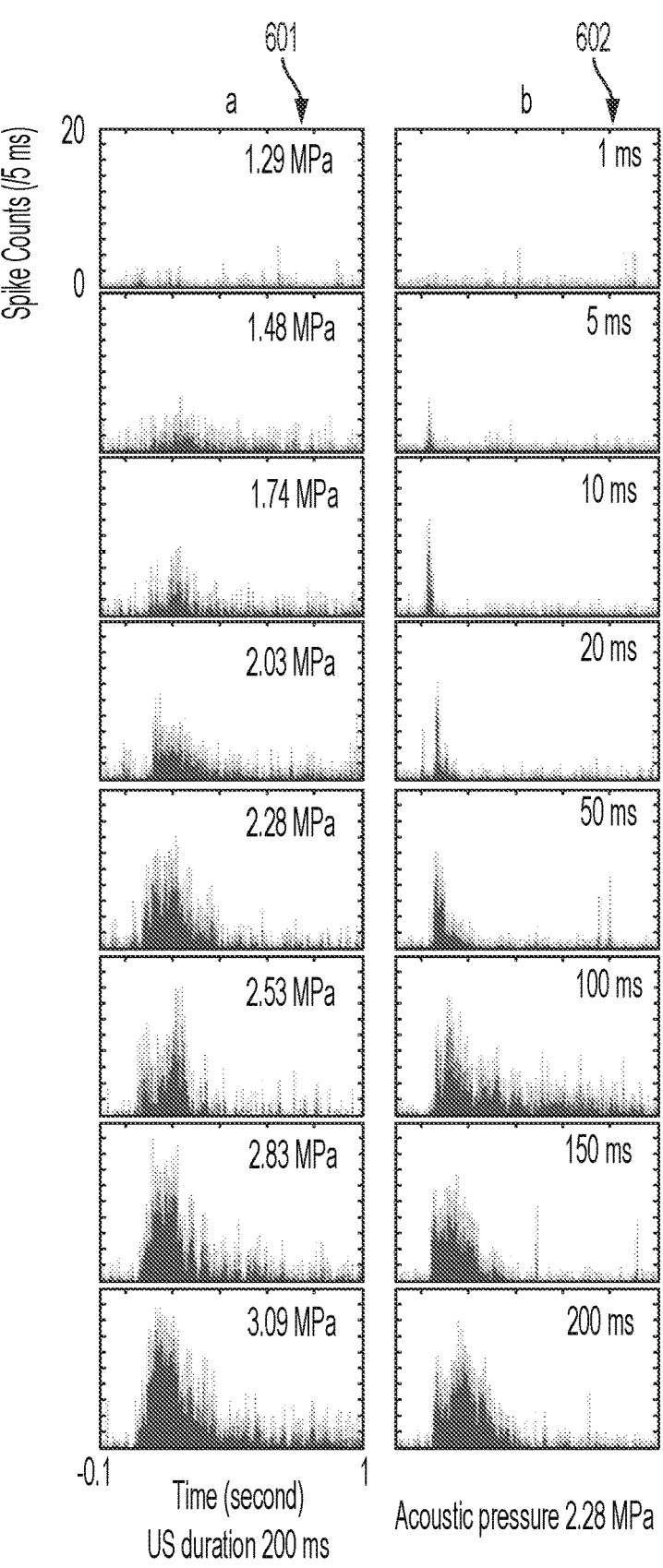
FIG. 6 shows an illustration of neural response under various ultrasound intensities, in accordance with various embodiments.
Figure 7A:
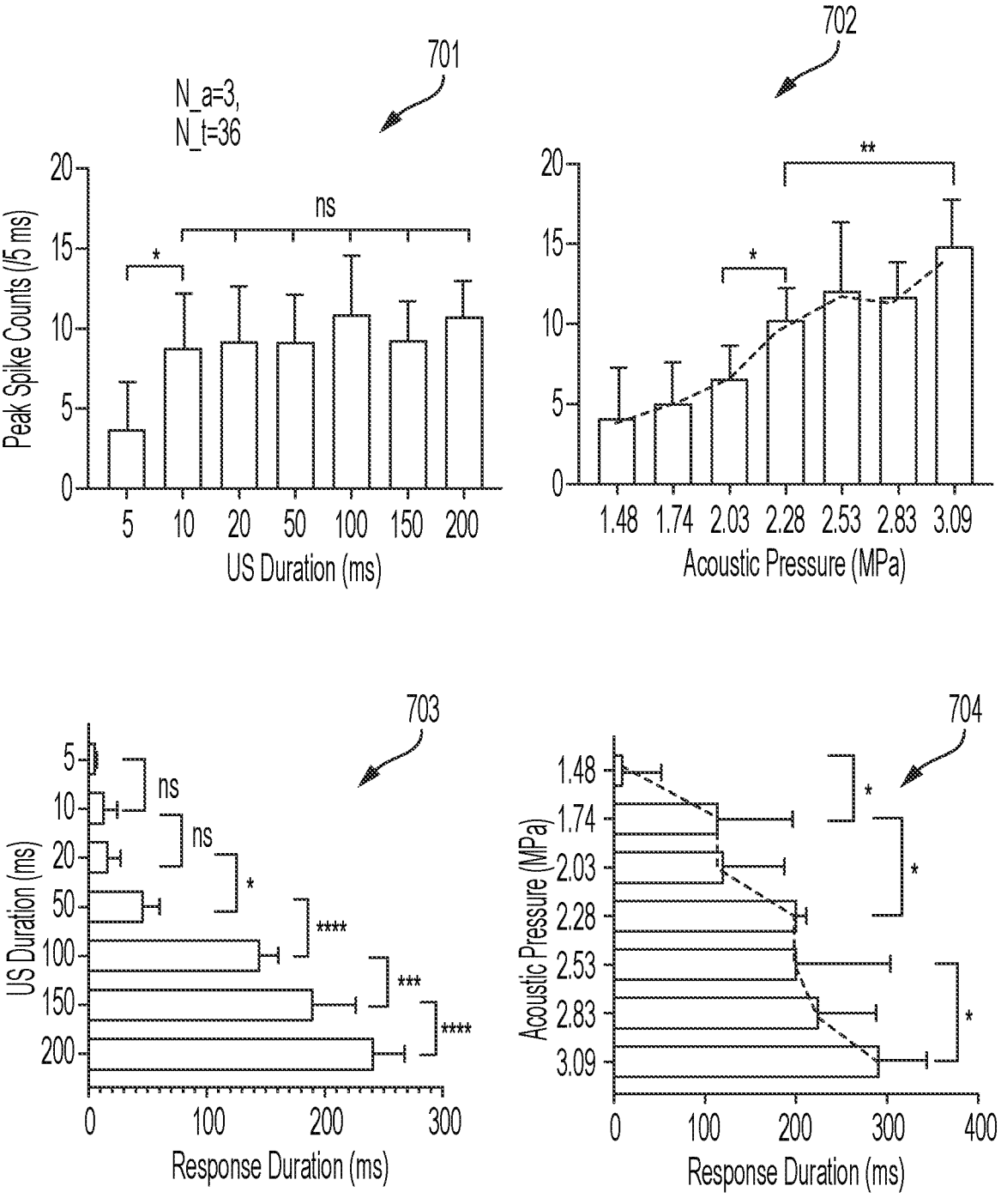
FIGS. 7A-B depict statistical comparisons among various ultrasound intensities and ultrasound durations evoking neural response, in accordance with various embodiments.
Figure 7B:
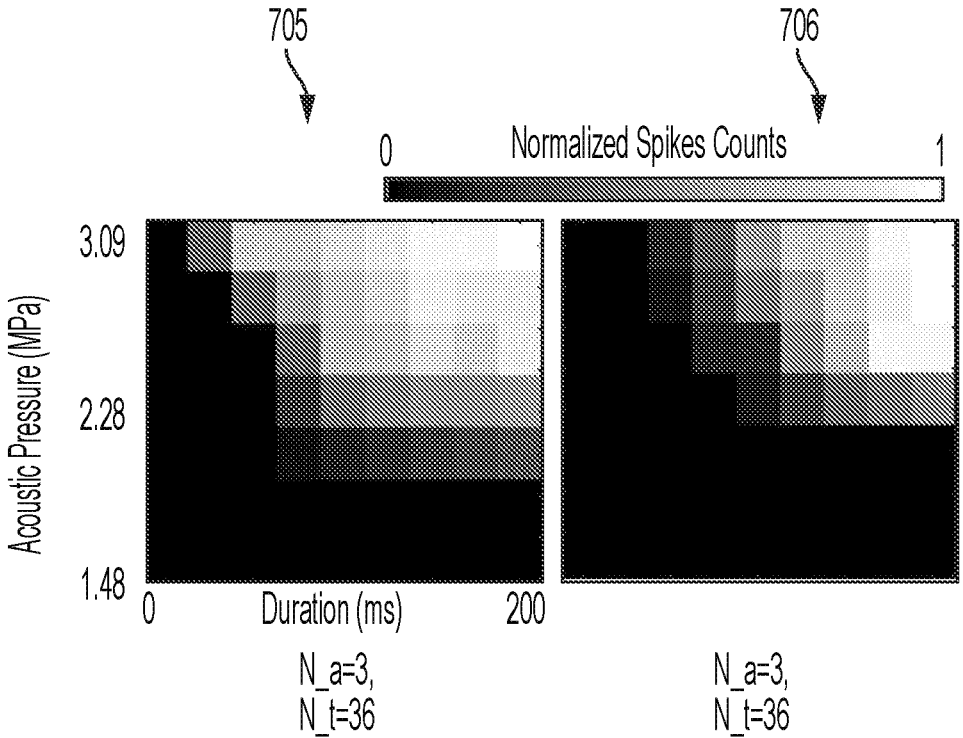
Figures 8A, 8B, 8C, 8D:
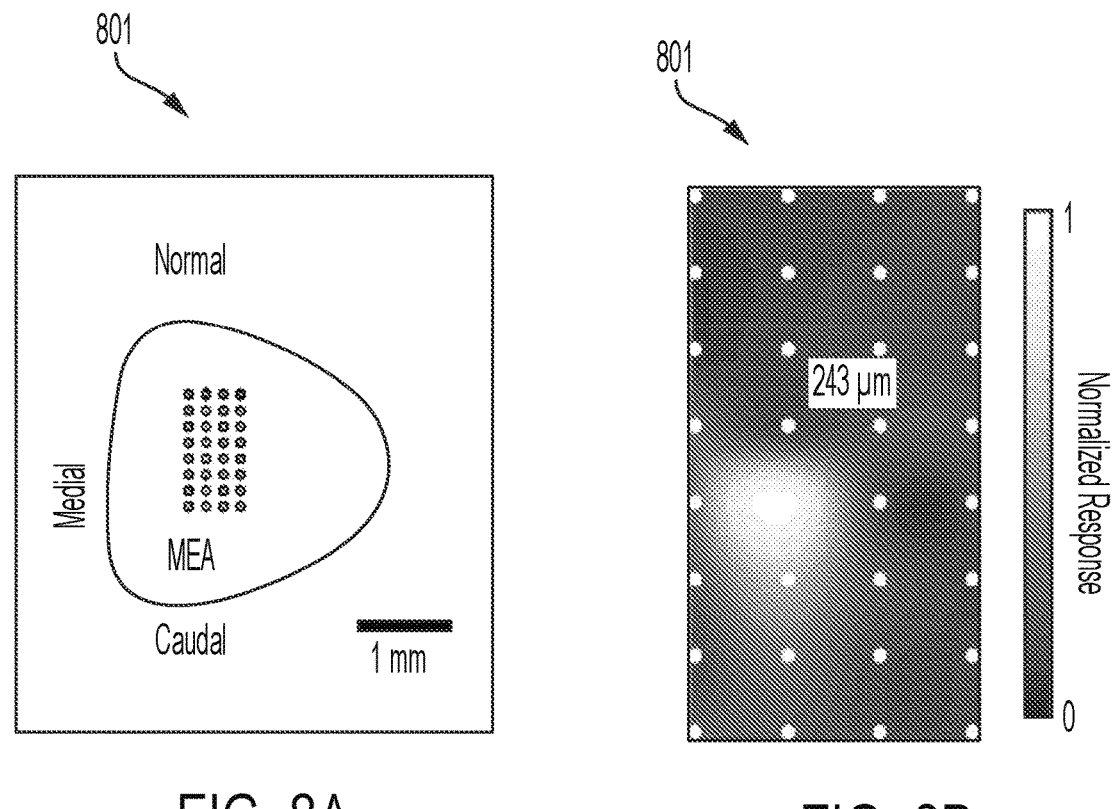
FIGS. 8A-D depicts a schematic diagram of a sensor used to monitor neural response to ultrasound stimulation and illustrations of associated sensed neural responses, in accordance with various embodiments.

FIG. 6 shows an illustration 601 of neural response under various ultrasound intensities. In addition, FIG. 6 shows an illustration 602 of neural response under various ultrasound durations from 1 ms to 200 ms. FIGS. 7A-B list the statistical comparisons among various ultrasound intensities and ultrasound durations on evoking neural response. All recordings were repeated 12 times for statistical analysis. For instance, FIG. 7A shows a comparison 701 of ultrasound duration to peak of spike counts, a comparison 702 of acoustic pressure to peak of spike counts, a comparison 703 of response duration to ultrasound duration, and a comparison 704 of response duration to acoustic pressure. N_a represents the number of animals used in this analysis (three) while N_t represents the repeated trials per each animal (thirty-six). FIG. 7B shows a map 705 for normal sighted rats comparing different acoustic pressures and durations to generated spike counts and a map 706 for blind rats comparing different acoustic pressures and durations to generated spike counts.

The quantifications of neural response were characterized by the response amplitude and the response duration respectively. It was observed that the response amplitude did not vary with 10 ms or longer ultrasound duration, but the response duration increased with the increase in ultrasound duration (FIG. 7A, chart 703). With respect to the increasing ultrasound intensity, both response amplitude and response duration were increased (FIG. 7A, chart 702, chart 704). In summary, the overall acoustic energy (that is the combination of ultrasound intensity and ultrasound duration) determined the threshold of evoking neural response. It was also found that the blind RCS rats have a higher stimulation threshold level (FIG. 7B, map 706) compared to the normal-sighted rats (FIG. 7B, map 705).

In addition, an investigation was performed of the performance of ultrasound stimulation on the basis of two sequence modes, including continuous tone burst mode and pulse mode with duty cycle. Both of these modes have the capability to stimulate the retina in vivo. Under the condition of the same time-averaged (that is, duty cycle×ultrasound duration) ultrasound sequence, there is no statistical difference on the total number of spikes. In particular, a higher duty cycle was able to generate a larger response amplitude while a lower duty cycle tended to maintain a longer response duration. These results implied that the ultrasound stimulation sequence has the potential to determine the response features.

FIGS. 8A-D depict a schematic diagram of a sensor used to monitor neural response to ultrasound stimulation and illustrations of associated sensed neural responses. FIGS. 8A-D include a schematic diagram 801 of a 32-channel MEA placed on the surface of SC, and a representative ultrasound stimulated response mapping 802 where the distance between each adjacent electrode (white dot) is 150 µm. FIGS. 8A-D include an illustration 803 of different positions of SC activated by controlling ultrasound stimulated retinal regions via moving the spherically focused transducer manually and a spatial resolution summary 804 over 3 RCS blind rats. N_t is the repeated trials per each rat (twelve).

The experiments further explore the spatial and temporal resolution of the retinal ultrasound stimulation in the SC. As regards the spatial resolution, the experiment reconstructed the distribution of ultrasound-evoked neural responses across the SC surface based on the response amplitude without changing the position of the ultrasound transducer, as shown in mapping 802. Then, the experiment included manually changing the positions of the ultrasound transducer using the 5-axis precision stage to validate the ability to activate different regions of the SC by shifting the focal point of ultrasound beam. As shown in illustration 803, the response pattern in the form of letter 'U' was observed in the SC, indicating that the ultrasound stimulated ROI of the retina activated the corresponding SC region. The activated SC regions varied with spatial resolution (defined as the averaged FWHM of medial and caudal directions) ranging from 161 µm to 299 µm. Such variation in spatial resolution could be attributed to the curvature of the retina since the ultrasound-induced retinal region could be different from the ultrasound beam pattern measured at the free space domain. Despite these variations, the ultrasound system still achieved a good spatial resolution at an average level of 250 µm on resolving the response patterns.

The temporal resolution of ultrasound stimulation (namely, frame rate) which was defined as the minimal frame interval capable of evoking stable neural response, is another important factor that can influence the functionality of a potential visual prosthesis. This factor could determine whether the visual prosthesis is able to provide a smooth vision for dynamic objects or not.

Figure 9:
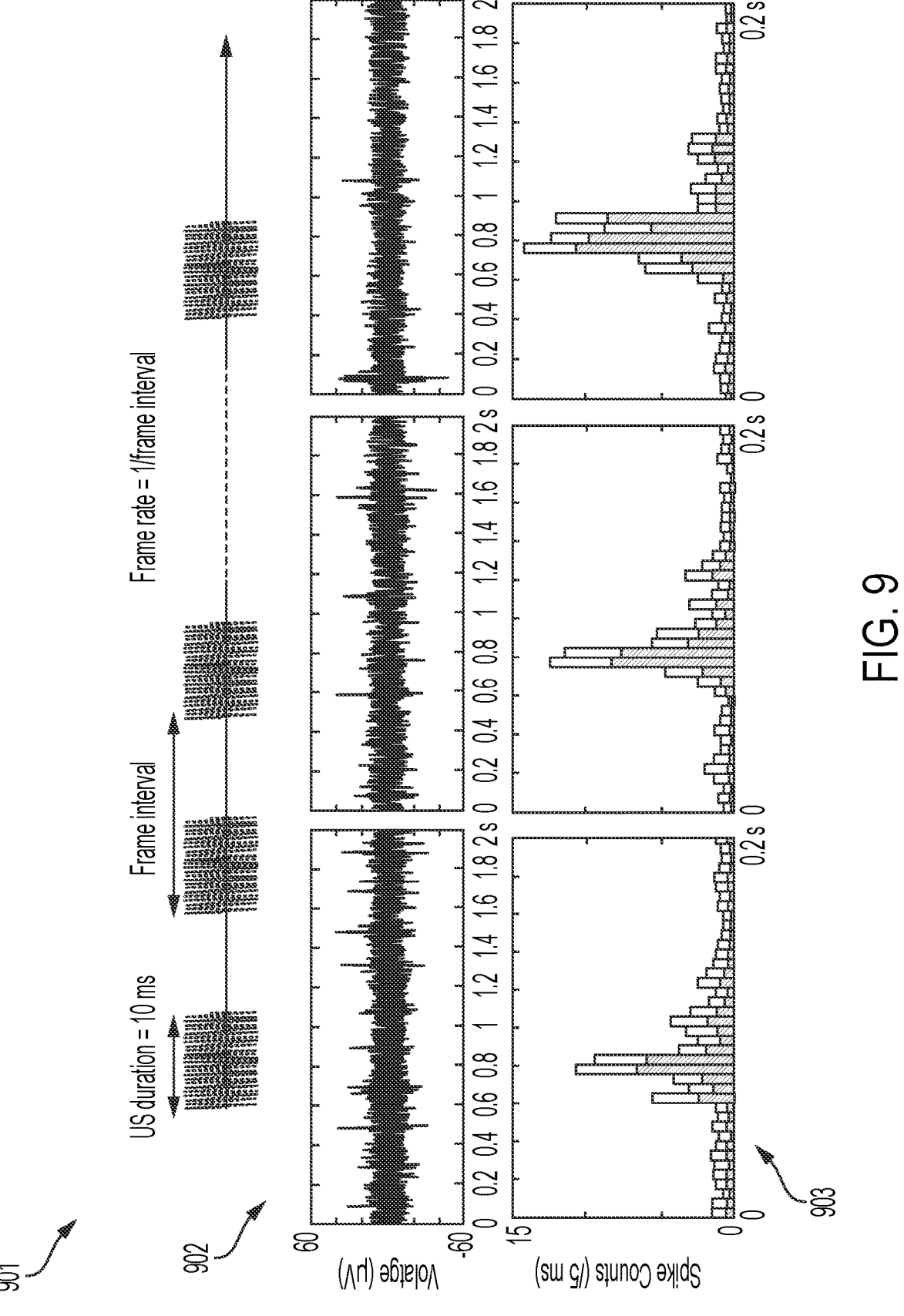
FIG. 9 depicts example ultrasound stimulation waveforms and sensed neural responses, in accordance with various embodiments.

With reference to FIG. 9, example ultrasound stimulation waveforms and sensed neural responses are illustrated. In various embodiments, consecutive 20-second ultrasound stimulations were conducted with different frame rates under the ultrasound parameter settings of 10-ms ultrasound duration and the 2.83 MPa NPP. As shown in FIG. 9, representative 2-second signals were randomly cropped from the 20 seconds raw data and spike counts recorded. Sequence 901 illustrates the implemented ultrasound stimulation sequence. Voltage charts 902 and spike counts 903 are viewed together and show, from left to right, the filtered raw signals and spike counts of the ultrasound response with the temporal resolution of 5 Hz, 2 Hz, and 1 Hz respectively.

Figure 10:
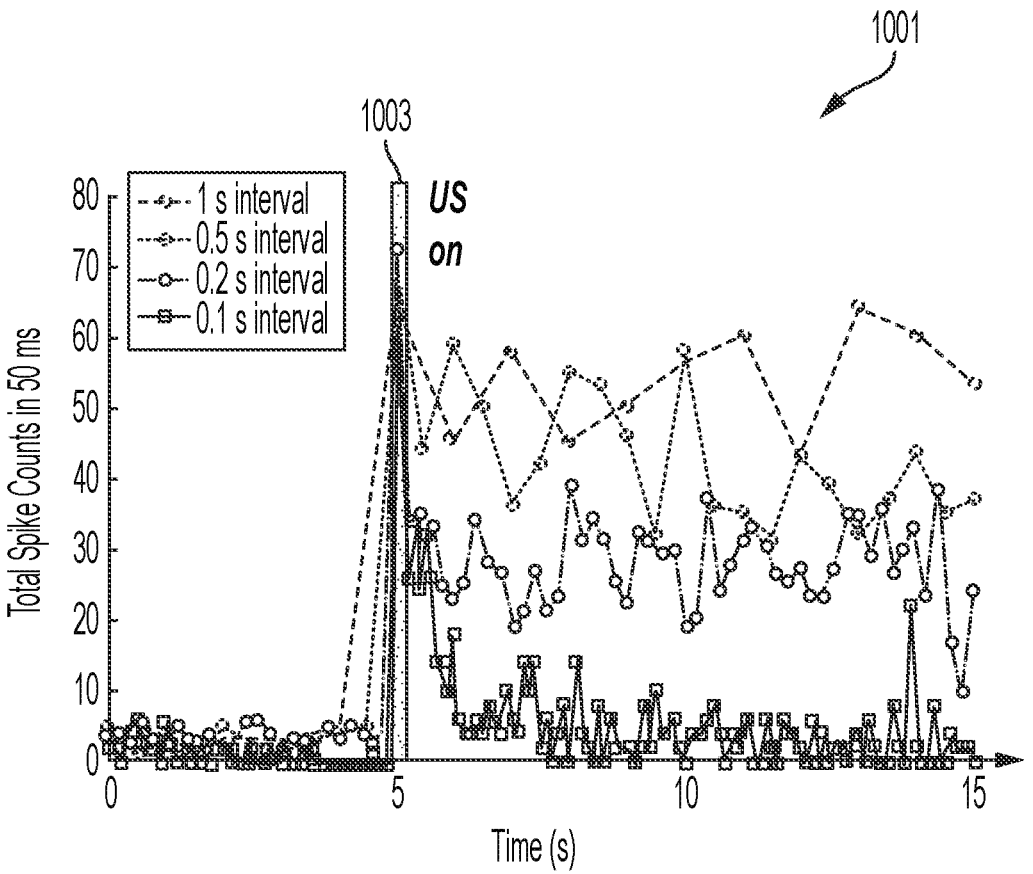
FIG. 10 depicts sensed neural responses for ultrasound stimulation waveforms having different on-off intervals, in accordance with various embodiments.

FIG. 10 depicts sensed neural responses for ultrasound stimulation waveforms having different on-off intervals. Spike counts 1001 reflect the total spike counts wherein the ultrasound stimulation switched from off to on. Notably ultrasound response remained stable until reaching the frame rate of 10 Hz.

Figure 11:
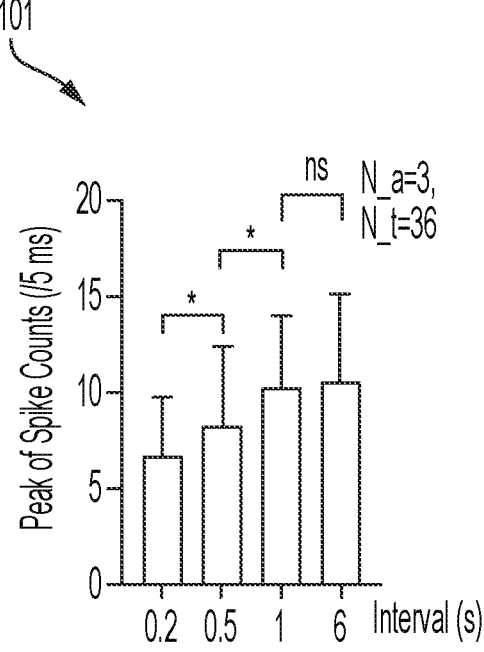
FIG. 11 depicts statistical representations of sensed neural responses for ultrasound stimulation waveforms compiled for repeated trials, in accordance with various embodiments.

FIG. 11 depicts statistical representations of sensed neural responses for ultrasound stimulation waveforms compiled for repeated trials. The chart 1005 shows statistical comparisons among various frame rates. It should be noted that N_a represents the number of animals used in this analysis while N_t represents the repeated trials per each animal. Referring to FIGS. 9, 10, and 11, results indicate that stable neural response were achieved up to the frame rate of 5 Hz, while a higher frame rate (e.g., 10 Hz) could potentially suppress the firing neurons in a short time (<5 seconds, shaded line 1003 in FIG. 10). These results are consistent with previous electrical stimulation experiments conducted in rats, which showed that suppression of the evoked responses in the SC was observed with increasing stimulus frequency.

To validate that such a suppression at higher frame rates was caused by neuron saturation rather than the neuron damage, there was performed an additional stimulation study at a lower frame rate to the same ROI right at the end of previous high frame rate stimulation. As a result, the similar levels of neural responses (response amplitude and response duration) were observed again, indicating that ultrasound stimulation at a high frame rate is safe.

Figure 12A:
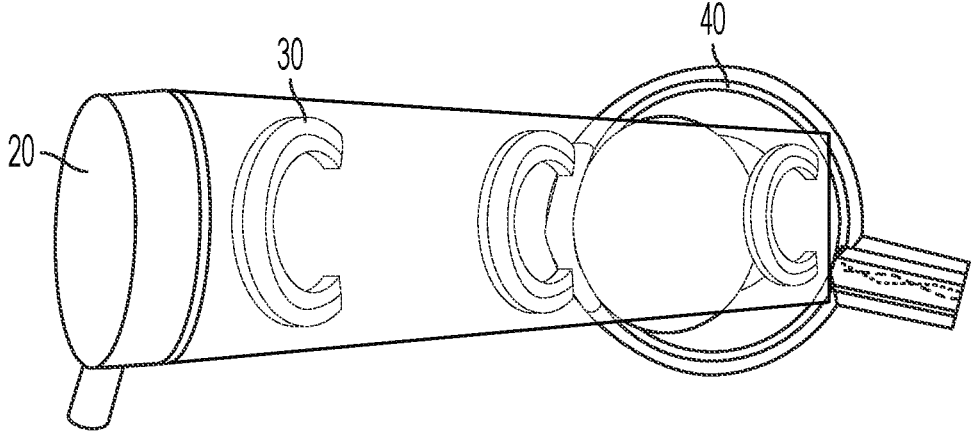
FIG. 12A depicts a helical transducer generating a 'C'-shaped beam pattern to ultrasonically stimulate an eye, in accordance with various embodiments.
Figure 12B:
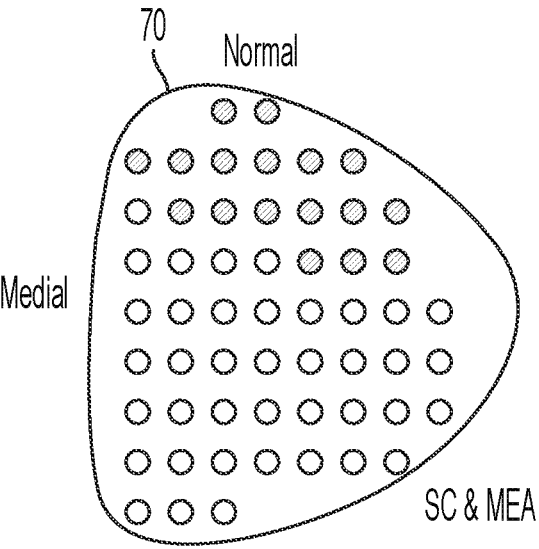
FIG. 12B depicts a sensor to detect neural responses to ultrasonic stimulation generated by the helical transducer of FIG. 12A, in accordance with various embodiments.
Figure 12C:
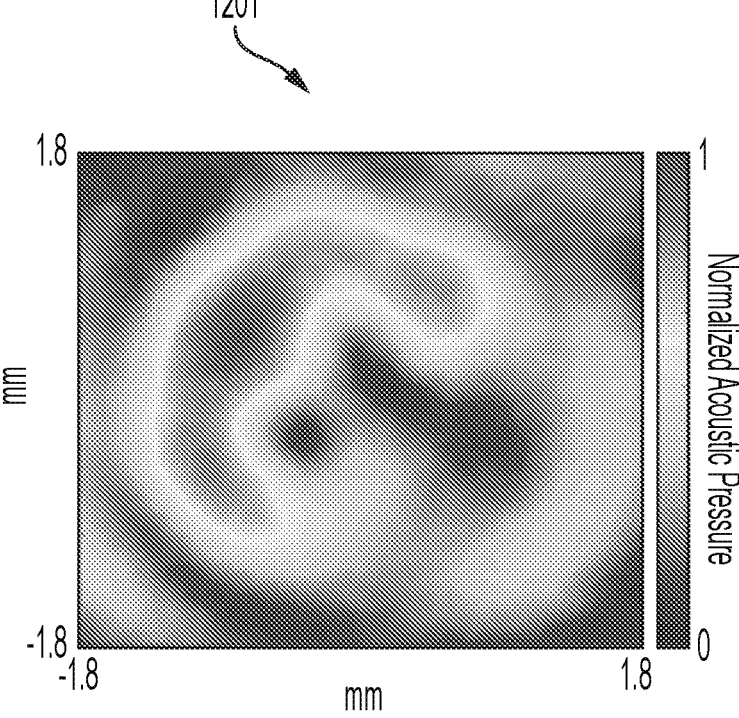
FIG. 12C illustrates normalized acoustic pressure generated by the ultrasound transducer of FIG. 12A, in accordance with various embodiments.
Figure 12D:
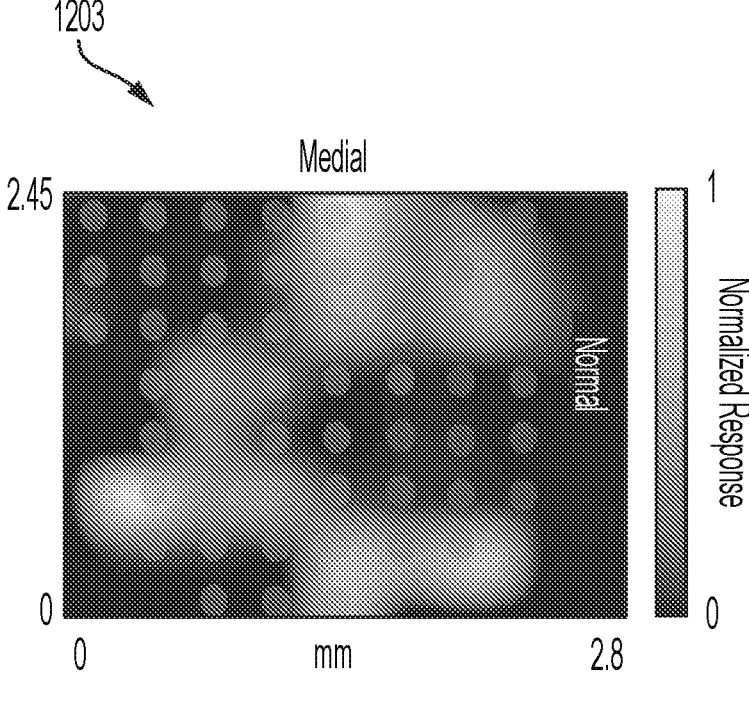
FIG. 12D illustrates a measured response pattern of ultrasound evoked neural response in response to stimulation by the transducer of FIG. 12A, in accordance with various embodiments.

With reference to FIG. 12A and owing to the single point beam shape of the spherically focused ultrasound transducer, in various embodiments, a novel helical transducer 20 is designed and fabricated in order to generate a specific beam pattern 30 of letter form—'C'. FIG. 12B depicts a sensor to detect neural responses to ultrasonic stimulation generated by the helical transducer of FIG. 12A. Different from the previous used 32-channel MEA with a 150 µm spacing to precisely calculate the spatial resolution of the ultrasound evoked neural response, herein is designed and implemented a brain activity sensor 74 comprising a 56-channel MEA with a 350 µm spacing to cover the whole SC region for better visualization of letter form—'C'. FIG. 12C illustrates normalized acoustic pressure generated by an ultrasound transducer and FIG. 12D illustrates a measured response pattern of ultrasound evoked neural response. As shown in FIGS. 12C-D an observed response pattern of ultrasound evoked neural response 1203 (The MEA recorded ultrasound evoked neural response at SC) was consistent with the measured normalized acoustic pattern generated by an ultrasound transducer as measured by a hydrophone (hydrophone results 1201 at the water condition). The hydrophone measured acoustic field with a pattern 'C' at focus, indicating that static ultrasound stimulation is able to create the same pattern of neural response in SC; specifically, the hydrophone measured acoustic field with a pattern 'C' at focus.

As an innovative strategy, systems and methods provided herein successfully demonstrate an extraocular ultrasound stimulation system that is capable of eliciting the neural response in a rat model of degenerative blindness. As a non-invasive, safe and cost-effective technology, direct ultrasound retinal stimulation may stimulate and generate response patterns at a spatial resolution level comparable to that of the first FDA approved retinal prosthesis—Argus II. In addition, our study demonstrates that the ultrasound stimulation technique can achieve good temporal resolution for the smooth transfer of the visual information, and also rules out the safety concerns for the implementation of ultrasound technique as a potential retinal prosthesis. To validate the capability of visual pattern generation, the embodiments herein include a helical ultrasound transducer and successfully demonstrated letter 'C' shape pattern by static ultrasound stimulation.

Owing to the fact that visual information is pre-processed in sub-cortical relay centers such as the SC (the rat SC receives projections from 85% to 90% of the retinal ganglion cells from the contralateral eye) and is finally processed in the VC, the experiments were designed to record neural response from both SC and VC. To establish the baseline of ultrasound stimulation, study was conducted in normal-sighted rats having healthy and functional photoreceptors to generate bioelectrical signals under natural light stimulation. As expected, robust light-evoked neural response were observed in both SC and VC. Comparable neural activity was also elicited during ultrasound stimulation indicating that ultrasound may, in various embodiment, generate encoded visual sequences.

To further illustrate the advantages of using ultrasound stimulation for visual restoration in blind subjects, the in vivo effectiveness of ultrasound stimulation was investigated in a rat model of degenerative blindness (RCS above 6 months of age) as discussed. With the loss of functional photoreceptors, light stimulation failed to evoke neural response in both SC and VC of RCS rats. By contrast, ultrasound stimulation was able to stimulate the retinal neurons, to evoke spike activities in the higher visual centers of the brain of blind RCS rats. This disclosure is a novel in vivo demonstration of ultrasound-based restoration of retinal function and the novel use of ultrasound as a non-invasive retinal prosthesis for clinical application to treat blindness.

In various embodiments, the disclosed systems and methods further exhibit safe bio-effects (e.g., thermal effect, cavitation effect are safe). First, the systems and methods were provided in connection with calculating the MI under all ultrasound parameters used. The ultrasound intensity and MI were within a reasonably safe range. Second, to assess whether ultrasound stimulation can damage retinal tissue, histology sections of the retina from the stimulated eyes were collected. Representative histology results of ultrasound stimulated retinas from both normal-sighted rat and retina degenerative rats were examined. The data suggested that the retina structure remain intact even after 2 hours of ultrasound stimulation. No obvious changes in the retinal architecture were noticed, confirming absence of damage to any of the retinal layers due to ultrasound stimulation.

Further analysis investigates the influence of changes in the ultrasound sequence on evoked neural response. By controlling the time-averaged ultrasound intensity and ultrasound duration, the response amplitude and response duration can be modified. The results demonstrate that, continuous ultrasound waves and pulsed ultrasound waves with various pulse repetition frequencies (PRF) can generate similar neural response on the basis of the same average power level. Such an observation (e.g., average power is important) agrees with in vitro retinal studies. However, in further embodiments, pulsed ultrasound with a PRF of 0.5-2 kHz range may be more effective than continuous wave in evoking neural response. In particular, the behavior response of Caenorhabditis elegans to ultrasound stimulation may depend on the PRF and duty cycle. Ideal parameters may be 1 kHz PRF and 50% duty cycle. The above differences could be attributed to species differences and associated differences in the types of neurons that were stimulated. Moreover, certain types of neuron cells or mechanosensitive ion channels (e.g., the auditory nerve fibers and hair cells) are selectively sensitive to the stimulation with specific frequency range.

Another important factor that related to the ultrasound sequence is the temporal resolution of ultrasound-evoked neural response. The temporal resolution could be increased when a more effective ultrasound retinal stimulation sequence is deployed. Although results have shown a frame rate of 5 Hz, higher frame rates are expected to be achievable, such as by using less powerful ultrasound.

Pulsed ultrasound stimulation may potentially activate auditory pathways and the corresponding responses may further spread to other cortical areas. Patients with earplugs may hear tones in the same frequency of Doppler ultrasound's repetitive frequency. To eliminate the potential auditory confounds, during the ultrasound stimulation experiments herein, the stimulation was initiated from the area of the auditory pathway. As expected, no stimulation-induced responses were observed in the above experiments. Moreover, SC mapping data (see FIGS. 8A-D) demonstrated that the neural response are confined to a small SC area presumably corresponding to the focal retina area that was stimulated. Therefore, it is confirmed that the neural response recorded from the SC and VC are the neural signals generated by the ultrasound-stimulated retina region.

The phenomena of delayed response and lower response amplitude observed in human patients are considered as the hallmarks of retinal degeneration diseases. Delayed response onset latency and reduced response amplitude during light stimulation were observed in various retinal degenerative rat models. In the present study, it was noted that, even in normal-sighted rats, the response onset latency for light stimulation (20.18+3.18 ms) was significantly shorter compared to ultrasound stimulation responses (43.88+9.55 ms, P<0.001). Based on previous light stimulation experiments conducted in normal rats, a direct correlation between the stimulus intensity and response onset latency was observed. The shorter response onset latency observed at higher light stimulation (0.81 log $cd/m^2$), was suggested to be due to the more rapid processing of the photic signals. According to these observations, an overall delay in the retina response during ultrasound stimulation can be related to the decreased stimulation effects. Other possible explanations for the delayed response include a slower response by the ultrasound-sensitive neurons compared to the light driven pathways or ultrasound-sensitive neurons require time to accumulate energy before reaching the threshold for activation. Another interesting finding of ultrasound stimulation is that the response onset latency of blind rats (86.68+18.98 ms) was significantly higher than that of normal-sighted rats (P<0.001). This can be attributed to the overall changes in the retinal homeostasis associated with prolonged visual deprivation or due to the remodeling taking place in the RCS retina during advanced disease conditions.

The current investigation on ultrasound neuromodulation mechanism includes two aspects, namely, a physical mechanism and a neuronal mechanism. Regarding the physical mechanism, acoustic radiation force (ARF), cavitation and thermal effect are major contributing factors. In particular, ultrasound-induced temperature increase is less than 2° C. at water condition (testing ultrasound parameters: 2.83 MPa NPP, 200 ms duration). On the basis that the temperature increase during in vivo condition should be even lower due to the blood flow perfusion, it is unlikely to evoke temperature-sensitive neurons. With respect to the cavitation effect, all MIs in studied were lower than the FDA-required threshold of 1.9 for diagnostic ultrasound imaging. Therefore, the cavitation effect could be neglected herein. As a consequence, and in some non-limiting embodiments, ARF is considered to be dominant of the physical mechanism of ultrasound stimulation, which is supported by the experimental results and ex vivo retina stimulation. ARF is a nonlinear effect that transfer the momentum from propagating waves to tissues. Specifically, ARF whose magnitude is determined by the temporal average intensity of the ultrasound and the absorption coefficient of the tissue $$ARF = \frac{2\alpha I}{c},$$

I is intensity, c is speed of sound in the medium, and $\alpha$ is the absorption coefficient) will lead to a mechanical displacement of tissue. Such a displacement could stretch or compress the cell membrane and cause the changes in membrane capacitance or the activation of mechanosensitive ion channels.

Various embodiments contemplate use of a 2D matrix array for retina stimulation. In comparison to a single-element ultrasound transducer with fixed beam pattern (that is, single point for spherically focused transducer, and letter—'C' for helical transducer) at a certain ROI, the implementation of 2D array has the following advantages. First, 2D array with the imaging capability may provide the potential guidance to precisely alter the focal zone along the retina with curvature, which maybe also benefit to reduce the ultrasound intensity level on evoking neural response. Second, a 2D array with the ability to electronically steer the beam in a 3D domain facilitates pattern generation such as arbitrary and dynamic patterns on the retina, which is practically useful in vision restoration. Finally, the anatomy of the eyeball, especially the cornea and lens in the anterior eye, may potentially affect the accuracy of the beam pattern generated in single-element ultrasound transducer. In other words, the reflection and refraction of ultrasound waves caused by these parts can distort the designed beam pattern. However, the ability of the array to independently control the amplitude and phase of each element can compensate for the distortion using inversion algorithms.

Finally, it is important to note that either the 3.1 MHz or 4.4 MHz transducer was primarily chosen in some embodiments based on two aspects. One is the compromise among in vivo feasibility, good spatial resolution and the capability of sustaining high ultrasound intensity and long ultrasound duration; the other is that the center frequency of ultrasound transducer ranging from 2 to 10 MHz could provide spatial resolution similar to that of the first FDA approved retinal prosthesis—Argus II. It has been well established that higher ultrasound frequency is associated with better spatial resolution, resulting in a more precise manner for retinal stimulation. However, the significant ultrasound attenuation and its potential thermal effect are factors at higher ultrasound frequency, especially when cornea and lens tissue are presented for in vivo study. Therefore, the selection of optimal ultrasound frequency with respect to the proper trade-off between ultrasound attenuation and spatial resolution may vary in different embodiments.

Having addressed various embodiments, further discussion of aspects of specific components of one embodiment of the system disclosed herein fur use with the studies conducted herein, follows below. In various embodiments, a dual-channel function generator (AFG3252C, Tektronix, Beaverton, OR, USA) is implemented to control the stimulus sequence and trigger signals for data acquisition. More specifically, the output of channel 1 may be used to generate the stimulus sequence, followed by an RF power amplifier (100A250A, Amplifier Research, Souderton, PA, USA) with a gain of 50 dB, and then used to drive a custom-build ultrasound transducer. The channel 2 which is self-synchronized with channel 1 through the internal system clock will send synchronized trigger signals to the interface board of an electrode recording system—Lablynx (Neuralynx, Bozeman, MT, USA). Regarding the light stimulation, a full-field strobe flash using a Grass Photic stimulator (Grass Instrument Co., W. Warwick, RI, USA) was delivered to the contralateral eye in the meanwhile the stimulator sends out a trigger signal to the Lablynx recording system for data recording. The time interval between each adjacent trigger signal is set to 6 seconds in order to ensure the evoked potential activity is back to normal.

To record multi-unit neural response (MUA) from the SC or VC, two micro-electrode arrays (MEA, Microprobes for Life Science, Gaithersburg, MD, USA) with an impedance of 0.5 Mega-Ohms were implemented. Specifically, the 32-channel (4 by 8) MEA with a finer spacing (150 μm) between adjacent electrodes was used to measure the spatial resolution of the ultrasound-evoked neural response. The 56-channel MEA with a spacing of 350 μm has larger recording area and thus can cover the whole surface of the SC. Such a design was used to record the ultrasound-evoked response pattern from SC. Signals from MEA were sampled at 30 kHz by the analog-to-digital multiplexing headstage (HS-32-MUX-PTB, Neuralynx) before transferring to the Lablynx recording system. The ultrasound transducer and the recording system were grounded together to minimize the artifacts.

Various ultrasound parameters and ultrasound sequences were used. Unless specified otherwise, the default ultrasound sequences were continuous waves with 100% duty cycle and a frame interval of 6 seconds. A six second interval was chosen to ensure the stimulated neurons fully recovered after each stimulation. The frame interval was also changed in evaluating temporal resolution of ultrasound-evoked neural response.

The relationships between acoustic pressure (that is NPP in this disclosure) and other ultrasound parameters such as MI, spatial peak pulse average intensity ($I_{SPPA}$) and spatial peak temporal average intensity ($I_{SPTA}$), are listed here:

$$MI = \frac{NPP(MPa)}{\sqrt{f(MHz)}}, \quad I_{SPPA} = \frac{NPP^2}{2\rho c},$$

$I_{SPTA} = I_{SPPA} \times$ Duty cycle, where $\rho$ and c are the density and sound speed in the medium.

To investigate the effect of ultrasound stimulation parameters on the evoked neural response, two stimulation parameters (ultrasound intensity and ultrasound duration) were explored. In terms of ultrasound intensity, various embodiments include changing the driving voltage (that is the output voltage of the function generator before fed into the power amplifier) from 50 mv to 500 mv with an interval of 50 mv. With respect to ultrasound duration, a test ranging from 50 ms to 200 ms with an interval of 50 ms was implemented.

To compare the continuous tone burst mode with pulse mode, four different stimulation sequences were evaluated, including one for continuous tone burst mode, and three for pulse mode with 30%, 50%, and 70% duty cycle, respectively.

The in vivo rat experiments were performed according to the University of Southern California Institutional Animal Care and Use Committee (IACUC) protocol. A total of 26 rats (male and around six-month old) were investigated, including 10 normally sighted Long-Evan (LE) rats and 16 RD Royal College of Surgeon (RCS) blind rats. The RCS rats are characterized by retinal pigment epithelium (RPE) dysfunction owing to the deletion of the Mer tyrosine kinase (MerTK) receptor that abolishes internalization of photoreceptor outer segments by RPE cells. For each rat, only one eye was used for stimulation purpose while the other eye was untreated.

Before the experiment, the rats were anaesthetized with an intraperitoneal injection of Ketamine/Xylazine (50-90 mg/kg, 5-10 mg/kg), and maintained under sevoflurane inhalation through a nose cone. For electrophysiological recording of the brain visual centers, a small craniotomy was made based on standard rat stereotactic co-ordinates to expose the VC. For the SC recording, the overlying VC was removed to expose the SC surface. The MEA was advanced into the VC and SC using the stereotactic apparatus. To ensure the sensitivity of the retina to light, all procedures were performed in a dark room illuminated with dim red light. During the experiment, the rat eye was first stimulated with light to establish the baseline of the retinal response, and then the de-gassed ultrasound gel was used to couple the space between transducer surface and rat eye, finally tested with ultrasound stimulation to investigate its potential benefits. After the experiment, the rats were sacrificed and both eyes (e.g., stimulated eye and the untreated eye) were kept for histology analysis in order to investigate the safety issue of our ultrasound stimulation sequence.

Considering the size and the potential ultrasound attenuation of the eye, an ultrasound transducer is fabricated comprising a 3.1 MHz transducer with a focal length of 10 mm and the f-number of 1. The DL-47 (Del-Piezo Specialties, FL, USA) material was used as the piezoelectric layer due to its high-power sustaining capability. A layer of 10-μm parylene was coated on the surface of the transducer for protection and insulation. During the experiment, the transducer was mounted on a 5-axis precision stage in order to accurately control the position of the transducer. The acoustic fields of the transducer were calibrated using a hydrophone (HGL-0085, ONDA Co, Sunnyvale, CA, USA). After obtaining the raw acoustic pressure signal data, the NPP, MI, spatial peak pulse average intensity ($I_{SPPA}$) were calculated.

With respect to the pattern generation experiment, a single-element helical transducer with a center frequency of 4.4 MHz was fabricated comprising 1-3 composite DL-48 (Del-Piezo Specialties, FL, USA) with the designed parameters of 4-mm outer diameter, 2-mm inner diameter, 10-mm focal length and 1.2-mm vertical separation.

The finite element analysis (FEA) simulation was conducted by COMSOL Multiphysics 5.3a (Stockholm, Sweden). Acoustic module and Bioheat transfer module were used in this study. In the simulation setup, the eyeball was defined at four main parts: cornea, lens, vitreous body and retina where the shape and size of each part was preset.

Two rat eyeballs were used to estimate the ultrasound attenuation caused by eye structure and the ultrasound-induced temperature increase. As regards to the ultrasound attenuation measurement, the hydrophone was placed at the focal point of the transducer (10 mm in depth). The intact eyeball was hold by a clip and placed on the top of the hydrophone with a gap about 1 mm. The acoustic pressure was repeatedly measured three times with and without the presence of eyeball, respectively. Regarding of the temperature measurement, a T-type wire thermocouple (XC-T-TC-WIRE, Omega Engineering Inc., CT, USA) was inserted into the posterior eye and then the temperature was read out from a thermocouple meter (RH820U, Omega Engineering Inc., CT, USA).

The raw electrode signals were sampled at 30 kHz and stored for post-processing in MATLAB 2019b (MathWorks). To obtain neuron spikes, a 500-7000 Hz band-pass filter were applied to SC data while VC data were filtered with a 300-7000 Hz band-pass filter. For SC and VC recording, a subpopulation of MEA channels that had strong background noise (presumably due to blood vessels) were manually deleted and excluded from final data analysis.

For each channel of the MEA, the maximal peaks with an amplitude three times stronger than the background noise of this channel are considered as spikes. The response was considered to be observed when the average spike counts per 5 ms was larger than 2. Response amplitude was defined as the peak of averaged spike counts per 5 ms. The response duration was defined by the time slot where the average spike counts per 5 ms was continuously larger than 2.

The total average spike counts in 500 ms of all channels over a time window of 500 ms were used to map the ultrasound-induced response distribution. In order to reconstruct the ultrasound-evoked response mapping at SC, 4-times modified Akima cubic 2-D interpolation was conducted. Since the response regions have irregular shapes, the spatial resolution of ultrasound-evoked neural response was determined as the averaged FWHM in the medial and caudal directions.

After the completion of the retina stimulation experiments, the rats were euthanized, eyes were either immersed in Bouin's fixative or embedded in paraffin. Transverse sections of the retina were cut, mounted on to slides, and stained with hematoxylin—eosin (H&E). A series of sections through the full extent of each transplant was evaluated at the light microscopic level.

Statistical significances between three or more were tested using ordinary one-way ANOVA and Tukey's multiple comparison test. Prism 9 software (GraphPad) was used to calculate the values. Significance values are $p<0.05$ (*), $p<0.01$ (), $p<0.001$ (*) and $p<0.0001$ (****).

Exemplary embodiments of the methods/systems have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:
1. A portable ultrasonic neuromodulation system for vision restoration from retinal diseases, the system comprising:
   a camera configured to capture an image;
   a processor configured to receive the captured image and to transfer data corresponding to the captured image to an ultrasound system; and
   the ultrasound system configured to convert the data corresponding to the image to an acoustic beam pattern corresponding to the image, the ultrasound system comprising an ultrasound transducer, wherein the ultrasound transducer is a helical ultrasonic transducer that delivers acoustic energy at a retina of an eye to evoke a neural response corresponding to the image, the acoustic energy generating or producing an acoustic beam pattern formed in a shape of a 'C', having a center frequency of between 3-24 MHz, and a negative peak acoustic pressure of between 0.5 MPa to 3 MPa for a duration of between 5 to 300 milliseconds.

2. The portable ultrasonic neuromodulation system according to claim 1, further comprising a sensor configured to monitor the neural response and provide data corresponding to the neural response to the processor.

3. The portable ultrasonic neuromodulation system according to claim 1, wherein the ultrasound transducer comprises a 2D matrix array of transducer elements.

4. The portable ultrasonic neuromodulation system according to claim 3, further comprising a power amplifier configured to drive each element of the 2D matrix array of the transducer elements.

5. A method for vision restoration from retinal diseases, the method comprising:

capturing, using a camera, an image;

receiving, at a processor, the captured image;

transferring, by the processor, the captured image to an ultrasound system including a helical ultrasonic transducer;

converting, by the ultrasound system, the captured image to an acoustic beam pattern; and transmitting, by the ultrasound system, the acoustic beam pattern to deliver energy to an eye, the acoustic beam pattern formed in a shape of a 'C', having a center frequency of between 3-24 MHz, and a negative peak acoustic pressure of between 0.5 MPa to 3 MPa for a duration of between 5 to 300 milliseconds, wherein the energy evokes neuron activity in a retina of the eye.

6. The method of claim 5, wherein the ultrasound system comprises a 2D matrix array of transducer elements, and wherein transmitting the acoustic beam pattern comprises modulating both amplitude and phase for each individual element of the 2D matrix array of transducer elements to produce the acoustic beam pattern.

7. The method of claim 6, wherein the ultrasound system comprises a power amplifier configured to drive each individual element of the 2D matrix array of transducer elements.

8. A portable ultrasonic neuromodulation system for vision restoration from retinal diseases, the system comprising:

a sensor configured to monitor a neural response of a brain;

a processor configured to generate an image and transfer data corresponding to the image to an ultrasound system; and the ultrasound system configured to convert the data corresponding to the image to an acoustic beam pattern corresponding to the image, the ultrasound system comprising a helical ultrasound transducer having a 2D matrix array of transducer elements, wherein the 2D matrix array of transducer elements generate an acoustic beam pattern formed in a shape of a 'C' and via modulation of both amplitude and phase information for each transducer element to deliver acoustic energy having a center frequency of between 3-24 MHz at a retina of an eye of a blind patient to evoke a neural response, and wherein the sensor measures the neural response and instructs the processor to alter the acoustic beam pattern to cause the neural response to correspond to the image.

9. The system of claim 8, wherein the transmitted acoustic beam pattern has a negative peak acoustic pressure of between 0.1 MPa to 15 MPa.

10. The system of claim 8, wherein the transmitted acoustic beam pattern is generated for a duration of between 0.1 to 500 milliseconds and with a duty cycle between 0.1% to 100%.

11. The system of claim 8, wherein the acoustic beam pattern has a negative peak acoustic pressure that is between 0.1 MPa to 15 MPa and is generated for a duration of between 0.1 to 500 milliseconds.

12. The system of claim 8, wherein the ultrasound system further comprises a power amplifier connected to and driving each transducer element of the 2D matrix array of transducer elements.

* * * * *